(12) United States Patent
Spitzer et al.

(10) Patent No.: US 9,815,882 B2
(45) Date of Patent: *Nov. 14, 2017

(54) TUMOR TARGETED TNF-RELATED APOPTOSIS INDUCING LIGAND FUSION POLYPEPTIDE, METHODS AND USES THEREFOR

(71) Applicant: Washington University, Saint Louis, MO (US)

(72) Inventors: Dirk Spitzer, Webster Groves, MO (US); William G Hawkins, Olivette, MO (US)

(73) Assignee: Washington University, Saint Louis, MO (US)

( * ) Notice: Subject to any disclaimer, the term of this patent is extended or adjusted under 35 U.S.C. 154(b) by 56 days.

This patent is subject to a terminal disclaimer.

(21) Appl. No.: 14/798,045

(22) Filed: Jul. 13, 2015

(65) Prior Publication Data

US 2017/0022263 A1    Jan. 26, 2017

Related U.S. Application Data

(63) Continuation of application No. 13/892,238, filed on May 10, 2013, now Pat. No. 9,127,081.

(60) Provisional application No. 61/645,058, filed on May 10, 2012.

(51) Int. Cl.

| | | |
|---|---|---|
| *C07K 14/52* | (2006.01) |
| *C07K 14/525* | (2006.01) |
| *C07K 14/705* | (2006.01) |
| *A61K 38/16* | (2006.01) |
| *A61K 38/17* | (2006.01) |
| *A61P 35/00* | (2006.01) |
| *C12N 15/09* | (2006.01) |
| *C12N 15/11* | (2006.01) |
| *C12N 15/62* | (2006.01) |
| *C12N 15/63* | (2006.01) |
| *C07K 14/47* | (2006.01) |
| *A61K 38/19* | (2006.01) |
| *C12N 15/70* | (2006.01) |
| *C12N 15/74* | (2006.01) |
| *C12N 15/79* | (2006.01) |
| *A61K 38/00* | (2006.01) |

(52) U.S. Cl.
CPC ............ *C07K 14/705* (2013.01); *A61K 38/17* (2013.01); *C07K 14/4747* (2013.01); *C07K 14/70575* (2013.01); *C12N 15/62* (2013.01); *C12N 15/63* (2013.01); *A61K 38/00* (2013.01); *A61K 38/177* (2013.01); *A61K 38/191* (2013.01); *C07K 14/525* (2013.01); *C07K 2319/00* (2013.01); *C07K 2319/21* (2013.01); *C07K 2319/33* (2013.01); *C07K 2319/43* (2013.01); *C07K 2319/74* (2013.01); *C12N 15/70* (2013.01); *C12N 15/74* (2013.01); *C12N 15/79* (2013.01)

(58) Field of Classification Search
CPC ........ A61K 38/00; A61K 38/17; A61K 38/16; A61K 38/18; A61K 38/19; A61K 38/191; C07K 2319/00; C07K 14/4747; C07K 14/525; C07K 14/705; C07K 2319/33; C07K 2319/21; C07K 2319/40; C12N 15/00; C12N 15/09; C12N 15/85; C12N 15/86; C12N 15/63; C12N 15/74; C12N 15/79; C12N 15/11; C12N 15/62
See application file for complete search history.

(56) References Cited

U.S. PATENT DOCUMENTS 8,461,311 B2 *  6/2013  Hawkins ............ C07K 14/4747
                                           530/300
9,127,081 B2 *  9/2015  Spitzer ................... A61K 38/17

FOREIGN PATENT DOCUMENTS

WO    WO-2010010051 A1 *  1/2010

OTHER PUBLICATIONS

Garg et al. Novel treatment option for MUC16-positive malignancies with the targeted TRAIL-based fusion protein Meso-TR3. BMC Cancer 14: 35, 2014 (12 total pages).*
Hawkins et al. A novel form of recombinant Trail as a platform technology to fight (pancreatic) cancer. J Surgical Res 158(2): p. 397, #55.20, 2010.*
Hung et al. A DNA vaccine encoding a single-chain trimer of HLA-A2 linked to human mesothelin peptide generates anti-tumor effects against human mesothelin-expressing tumors. Vaccine 25: 127-135, 2007.*
Schneider et al. Potent antitumoral activity of TRAIL through generation of tumor-targeted single-chain fusion proteins. Cell Death Dis 1(8): e68, 2010 (17 total pages).*
Spitzer et al. Trail is sterically incapable of engaging death receptors in an autocrine fashion: implications for Trail-based cancer immunotherapies. Abstracts for the 26th Annual Scientific Meeting of the Society for Immunotherapy of Cancer; Nov. 4-6, 2011; Abstract #145.*
Spitzer et al. A genetically encoded multifunctional TRAIL trimer facilitates cell-specific targeting and tumor cell killing. Mol Cancer Ther 9(7): 2142-2151, 2010.*
Su et al. Mesothelin's minimal MUC16 binding moiety converts TR3 into a potent cancer therapeutic via hierarchical binding events at the plasma membrane. Oncotarget 7(21): 31534-31549, 2016.*

* cited by examiner

*Primary Examiner* — Bridget E Bunner
(74) *Attorney, Agent, or Firm* — Saul L. Zackson; Zackson Law LLC

(57) ABSTRACT

Fusion polypeptides comprising a TRAIL trimer and a targeting domain are disclosed. The targeting domain can be, in some embodiments, a sequence that binds MUC16, which is prevalent on some tumor cells such as pancreatic and ovarian tumor cells. A sequence that binds MUC 16 can be mesothelin or a MUC16-binding fragment thereof, such as amino acids 1-64 of mesothelin. A fusion polypeptide of the present teachings can induce apoptosis in a target cell such as a MUC16-expressing cancer cell. Also disclosed are nucleic acids encoding the fusion polypeptides, and methods of use of the fusion polypeptides and nucleic acids.

18 Claims, 14 Drawing Sheets
(5 of 14 Drawing Sheet(s) Filed in Color)

FIG. 4B *soluble mesothelin* 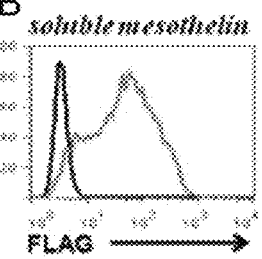
FIG. 4C *Meso-TR3* 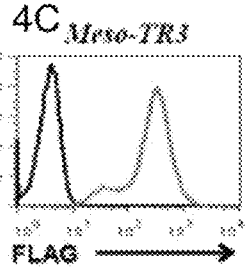
FIG. 4D
*MUC16* 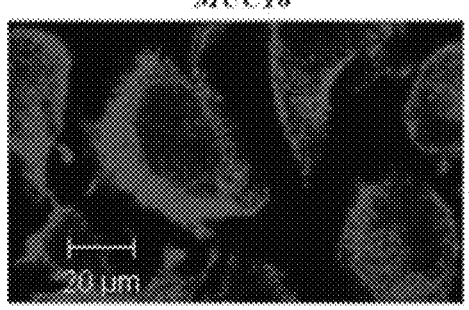
*FLAG* 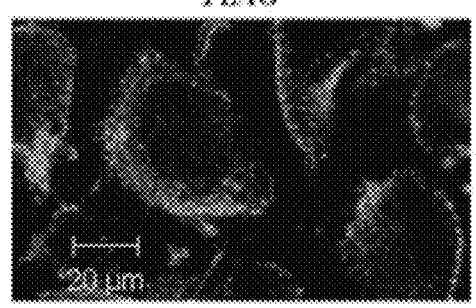
*TOPRO3* 
*Merge* 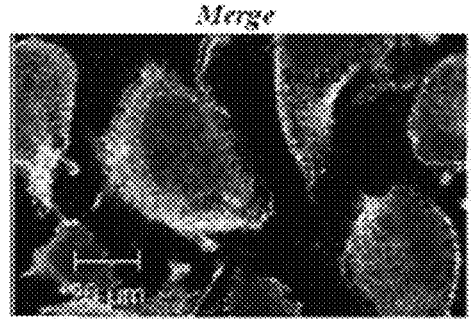

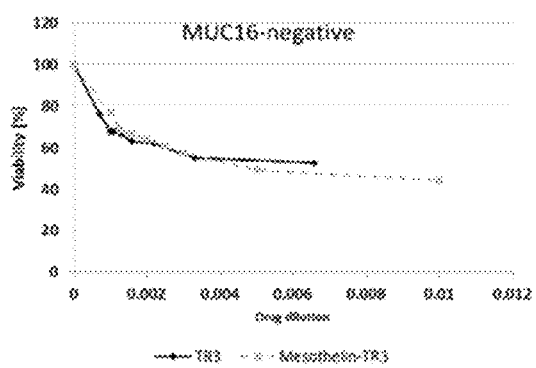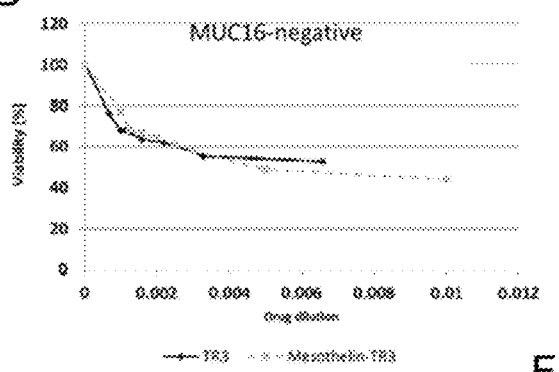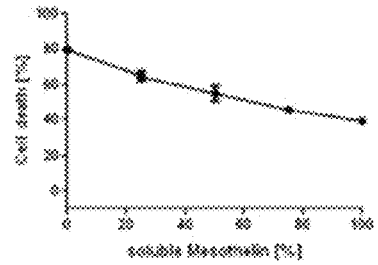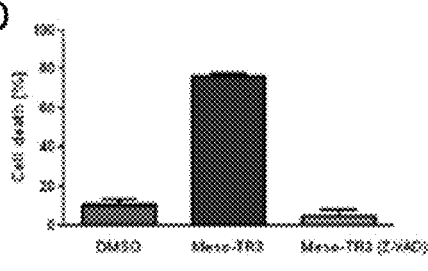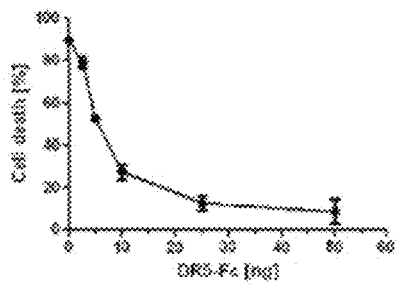

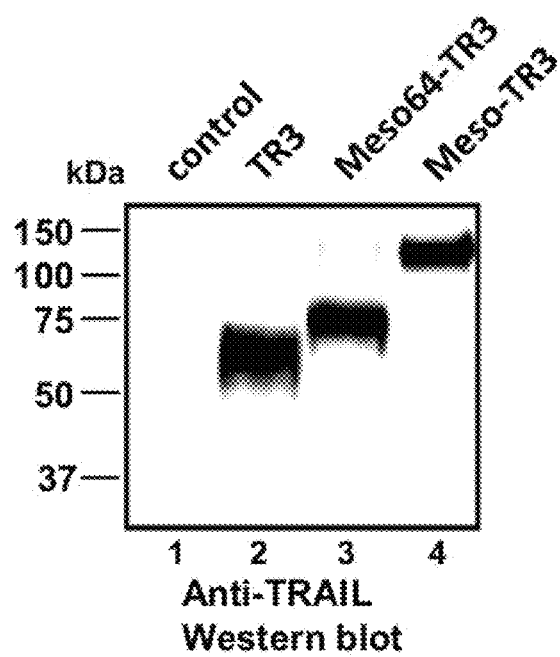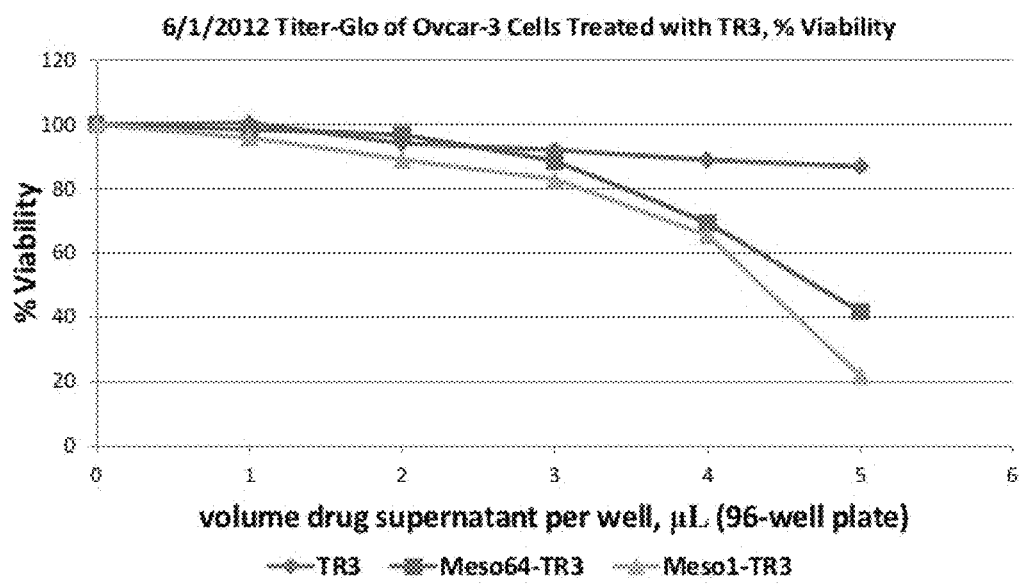
FIG. 14

SEQUENCE LISTING

```
<160> NUMBER OF SEQ ID NOS: 4

<210> SEQ ID NO 1
<211> LENGTH: 191
<212> TYPE: PRT
<213> ORGANISM: Homo sapiens

<400> SEQUENCE: 1

Met Ile Leu Arg Thr Ser Glu Glu Thr Ile Ser Thr Val Gln Glu Lys
1               5                   10                  15

Gln Gln Asn Ile Ser Pro Leu Val Arg Glu Arg Gly Pro Gln Arg Val
            20                  25                  30

Ala Ala His Ile Thr Gly Thr Arg Gly Arg Ser Asn Thr Leu Ser Ser
        35                  40                  45

Pro Asn Ser Lys Asn Glu Lys Ala Leu Gly Arg Lys Ile Asn Ser Trp
    50                  55                  60

Glu Ser Ser Arg Ser Gly His Ser Phe Leu Ser Asn Leu His Leu Arg
65                  70                  75                  80

Asn Gly Glu Leu Val Ile His Glu Lys Gly Phe Tyr Tyr Ile Tyr Ser
                85                  90                  95

Gln Thr Tyr Phe Arg Phe Gln Glu Glu Ile Lys Glu Asn Thr Lys Asn
            100                 105                 110

Asp Lys Gln Met Val Gln Tyr Ile Tyr Lys Tyr Thr Ser Tyr Pro Asp
        115                 120                 125

Pro Ile Leu Leu Met Lys Ser Ala Arg Asn Ser Cys Trp Ser Lys Asp
    130                 135                 140

Ala Glu Tyr Gly Leu Tyr Ser Ile Tyr Gln Gly Gly Ile Phe Glu Leu
145                 150                 155                 160

Lys Glu Asn Asp Arg Ile Phe Val Ser Val Thr Asn Glu His Leu Ile
                165                 170                 175

Asp Met Asp His Glu Ala Ser Phe Phe Gly Ala Phe Leu Val Gly
            180                 185                 190
```

<210> SEQ ID NO 2
<211> LENGTH: 6113
<212> TYPE: DNA
<213> ORGANISM: Artificial Sequence
<220> FEATURE:
<223> OTHER INFORMATION: plasmid encoding fusion polypeptide

<400> SEQUENCE: 2

| | | | | | |
|---|---|---|---|---|---|
| gtcgacttct | gaggcggaaa | gaaccagctg | tggaatgtgt | gtcagttagg | gtgtggaaag | 60 |
| tccccaggct | ccccagcagg | cagaagtatg | caaagcatgc | atctcaatta | gtcagcaacc | 120 |
| aggtgtggaa | agtccccagg | ctccccagca | ggcagaagta | tgcaaagcat | gcatctcaat | 180 |
| tagtcagcaa | ccatagtccc | gcccctaact | ccgcccatcc | cgcccctaac | tccgcccagt | 240 |
| tccgcccatt | ctccgcccca | tggctgacta | attttttta | tttatgcaga | ggccgaggcc | 300 |
| gcctcggcct | ctgagctatt | ccagaagtag | tgaggaggct | tttttggagg | cctaggcttt | 360 |
| tgcaaaaagc | tggatcgatc | ctgagaactt | cagggtgagt | ttggggaccc | ttgattgttc | 420 |
| tttcttttc | gctattgtaa | aattcatgtt | atatggaggg | gcaaagtttt | caggggtgtt | 480 |
| gtttagaatg | gaagatgtc | ccttgtatca | ccatggaccc | tcatgataat | tttgtttctt | 540 |
| tcactttcta | ctctgttgac | aaccattgtc | tcctcttatt | tcttttcat | tttctgtaac | 600 |
| tttttcgtta | aactttagct | tgcatttgta | acgaattttt | aaattcactt | ttgtttattt | 660 |
| gtcagattgt | aagtactttc | tctaatcact | tttttttcaa | ggcaatcagg | gtatattata | 720 |
| ttgtacttca | gcacagtttt | agagaacaat | tgttataatt | aaatgataag | gtagaatatt | 780 |
| tctgcatata | aattctggct | ggcgtggaaa | tattcttatt | ggtagaaaca | actacatcct | 840 |
| ggtcatcatc | ctgcctttct | ctttatggtt | acaatgatat | acactgtttg | agatgaggat | 900 |
| aaaatactct | gagtccaaac | cgggcccctc | tgctaaccat | gttcatgcct | tcttcttttt | 960 |
| cctacagctc | ctgggcaacg | tgctggttat | tgtgctgtct | catcattttg | gcaaagaatt | 1020 |
| gtaatacgac | tcactatagg | gcgaattcag | gttctgtgga | caatcacaat | gggaatccaa | 1080 |
| ggagggtctg | tcctgttcgg | gctgctgctc | gtcctggctg | tcttctgcca | ttcaggtcat | 1140 |
| agcctgcaga | gctacaaccc | tccgcgtacg | gactacaagg | acgatgatga | caaacagatc | 1200 |
| agcggtggag | gctcagaagt | ggagaagaca | gcctgtcctt | caggcaagaa | ggcccgcgag | 1260 |
| atagacgaga | gcctcatctt | ctacaagaag | tgggagctgg | aagcctgcgt | ggatgcggcc | 1320 |
| ctgctggcca | cccagatgga | ccgcgtgaac | gccatcccct | tcacctacga | gcagctggac | 1380 |
| gtcctaaagc | ataaactgga | tgagctcggt | ggaggctcag | gtacgccacc | tatgattttg | 1440 |
| agaacctctg | aggaaaccat | ttctacagtt | caagaaaagc | aacaaaatat | ttctccccta | 1500 |
| gtgagagaaa | gaggtcctca | gagagtagca | gctcacataa | ctgggaccag | aggaagaagc | 1560 |
| aacacattgt | cttctccaaa | ctccaagaat | gaaaaggctc | tgggccgcaa | aataaactcc | 1620 |
| tgggaatcat | caaggagtgg | gcattcattc | ctgagcaact | gcacttgag | aatggtgaa | 1680 |
| ctggtcatcc | atgaaaaagg | gttttactac | atctattccc | aaacatactt | tcgatttcag | 1740 |
| gaggaaataa | agaaaacac | aaagaacgac | aaacaatgg | tccaatatat | ttacaaatac | 1800 |
| acaagttatc | ctgaccctat | attgttgatg | aaaagtgcta | gaatagttg | ttggtctaaa | 1860 |
| gatgcagaat | atggactcta | ttccatctat | caaggggaa | tatttgagct | taaggaaaat | 1920 |
| gacagaattt | tgtttctgt | aacaaatgag | cacttgatag | acatggacca | tgaagccagt | 1980 |
| ttttttcgggg | ccttttttagt | tggcagatcc | caaaatattt | ctcccctagt | gagagaaaga | 2040 |
| ggtcctcaga | gagtagcagc | tcacataact | gggaccagag | aagaagcaa | cacattgtct | 2100 |

```
tctccaaact ccaagaatga aaaggctctg ggccgcaaaa taaactcctg ggaatcatca    2160
aggagtgggc attcattcct gagcaacttg cacttgagga atggtgaact ggtcatccat    2220 gaaaagggt tttactacat ctattcccaa acatactttc gatttcagga ggaaataaaa     2280 gaaacacaa agaacgacaa acaaatggtc aatatatttt acaaatacac aagttatcct     2340
gaccctatat tgttgatgaa aagtgctaga aatagttgtt ggtctaaaga tgcagaatat    2400
ggactctatt ccatctatca agggggaata tttgagctta aggaaaatga cagaattttt    2460
gtttctgtaa caaatgagca cttgatagac atggaccatg aagccagttt tttcggggcc    2520
tttttagttg gcagatccca ccaccaccac caccaccaaa atatttctcc cctagtgaga    2580
gaaagaggtc ctcagagagt agcagctcac ataactggga ccagaggaag aagcaacaca    2640
ttgtcttctc caaactccaa gaatgaaaag gctctgggcc gcaaaataaa ctcctgggaa    2700
tcatcaagga gtgggcattc attcctgagc aacttgcact tgaggaatgg tgaactggtc    2760
atccatgaaa aagggtttta ctacatctat tcccaaacat actttcgatt tcaggaggaa    2820 ataaagaaa acacaagaa cgacaaacaa atggtccaat atatttacaa atacacaagt     2880
tatcctgacc ctatattgtt gatgaaaagt gctagaaata gttgttggtc taaagatgca    2940
gaatatggac tctattccat ctatcaaggg ggaatatttg agcttaagga aaatgacaga    3000 attttttgttt ctgtaacaaa tgagcacttg atagacatgg accatgaagc cagttttttc    3060 ggggccttttt agttggcag atcttaatct aggatcttat taaagcagaa cttgtttatt    3120
gcagcttata tggttacaa ataaagcaat agcatcacaa atttcacaaa taaagcattt     3180
ttttcactgc attctagttg tggtttgtcc aaactcatca atgtatctta tcatgtctgg    3240
tcgactctag actcttccgc ttcctcgctc actgactcgc tgcgctcggt cgttcggctg    3300
cggcgagcgg tatcagctca ctcaaaggcg gtaatacggt tatccacaga atcaggggat    3360
aacgcaggaa agaacatgtg agcaaaaggc cagcaaaagg ccaggaaccg taaaaaggcc    3420
gcgttgctgg cgtttttcca taggctccgc ccccctgacg agcatcacaa aaatcgacgc    3480
tcaagtcaga ggtggcgaaa cccgacagga ctataaagat accaggcgtt tccccctgga    3540
agctccctcg tgcgctctcc tgttccgacc ctgccgctta ccggatacct gtccgccttt    3600
ctcccttcgg gaagcgtggc gctttctcaa tgctcacgct gtaggtatct cagttcggtg    3660
taggtcgttc gctccaagct gggctgtgtg cacgaacccc ccgttcagcc cgaccgctgc    3720
gccttatccg gtaactatcg tcttgagtcc aacccggtaa gacacgactt atcgccactg    3780
gcagcagcca ctggtaacag gattagcaga gcgaggtatg taggcggtgc tacagagttc    3840
ttgaagtggt ggcctaacta cggctacact agaaggacag tatttggtat ctgcgctctg    3900
ctgaagccag ttaccttcgg aaaaagagtt ggtagctctt gatccggcaa acaaaccacc    3960
gctggtagcg gtggtttttt tgtttgcaag cagcagatta cgcgcagaaa aaaggatct    4020 caagaagatc ctttgatctt ttctacgggg tctgacgctc agtggaacga aaactcacgt    4080
taagggattt tggtcatgag attatcaaaa aggatcttca cctagatcct tttaaattaa    4140
aaatgaagtt ttaaatcaat ctaaagtata tatgagtaaa cttggtctga cagttaccaa    4200
tgcttaatca gtgaggcacc tatctcagcg atctgtctat ttcgttcatc catagttgcc    4260
tgactccccg tcgtgtagat aactacgata cgggagggct taccatctgg ccccagtgct    4320
gcaatgatac cgcgagaccc acgctcaccg gctccagatt tatcagcaat aaaccagcca    4380
gccgaagggg ccgagcgcag aagtggtcct gcaactttat ccgcctccat ccagtctatt    4440
aattgttgcc gggaagctag agtaagtagt tcgccagtta atagtttgcg caacgttgtt    4500
```

| | |
|---|---|
| gccattgcta caggcatcgt ggtgtcacgc tcgtcgtttg gtatggcttc attcagctcc | 4560 |
| ggttcccaac gatcaaggcg agttacatga tcccccatgt tgtgcaaaaa agcggttagc | 4620 |
| tccttcggtc ctccgatcgt tgtcagaagt aagttggccg cagtgttatc actcatggtt | 4680 |
| atggcagcac tgcataattc tcttactgtc atgccatccg taagatgctt ttctgtgact | 4740 |
| ggtgagtact caaccaagtc attctgagaa tagtgtatgc ggcgaccgag ttgctcttgc | 4800 |
| ccggcgtcaa tacgggataa taccgcgcca catagcagaa ctttaaaagt gctcatcatt | 4860 |
| ggaaaacgtt cttcggggcg aaaactctca aggatcttac cgctgttgag atccagttcg | 4920 |
| atgtaaccca ctcgtgcacc caactgatct tcagcatctt ttactttcac cagcgtttct | 4980 |
| gggtgagcaa aaacaggaag gcaaaatgcc gcaaaaaagg gaataagggc gacacggaaa | 5040 |
| tgttgaatac tcatactctt cctttttcaa tattattgaa gcatttatca gggttattgt | 5100 |
| ctcatgagcg gatacatatt tgaatgtatt tagaaaaata aacaaatagg ggttccgcgc | 5160 |
| acatttcccc gaaaagtgcc acctgacgtc taagaaacca ttattatcat gacattaacc | 5220 |
| tataaaaata ggcgtatcac gaggcccctt tcgtctcgcg cgtttcggtg atgacggtga | 5280 |
| aaacctctga cacatgcagc tcccggagac ggtcacagct tgtctgtaag cggatgccgg | 5340 |
| gagcagacaa gcccgtcagg gcgcgtcagc gggtgttggc gggtgtcggg gctggcttaa | 5400 |
| ctatgcggca tcagagcaga ttgtactgag agtgcaccat atgcggtgtg aaataccgca | 5460 |
| cagatgcgta aggagaaaat accgcatcag gaaattgtaa acgttaatat tttgttaaaa | 5520 |
| ttcgcgttaa attttttgtta atcagctca ttttttaacc aataggccga atcggcaaa | 5580 |
| atcccttata aatcaaaaga atagaccgag atagggttga gtgttgttcc agtttggaac | 5640 |
| aagagtccac tattaaagaa cgtggactcc aacgtcaaag ggcgaaaaac cgtctatcag | 5700 |
| ggcgatggcc cactacgtga accatcaccc taatcaagtt ttttggggtc gaggtgccgt | 5760 |
| aaagcactaa atcggaaccc taaagggagc ccccgattta gagcttgacg ggaaagccg | 5820 |
| gcgaacgtgg cgagaaagga agggaagaaa gcgaaaggag cgggcgctag gcgctggca | 5880 |
| agtgtagcgg tcacgctgcg cgtaaccacc acaccgccg cgcttaatgc gccgctacag | 5940 |
| ggcgcgtcgc gccattcgcc attcaggcta cgcaactgtt gggaagggcg atcggtgcgg | 6000 |
| gcctcttcgc tattacgcca gctggcgaag gggggatgtg ctgcaaggcg attaagttgg | 6060 |
| gtaacgccag ggttttccca gtcacgacgt tgtaaaacga cggccagtga att | 6113 |

<210> SEQ ID NO 3
<211> LENGTH: 6767
<212> TYPE: DNA
<213> ORGANISM: Artificial Sequence
<220> FEATURE:
<223> OTHER INFORMATION: plasmid encoding fusion polypeptide

<400> SEQUENCE: 3

| | |
|---|---|
| gtcgacttct gaggcggaaa gaaccagctg tggaatgtgt gtcagttagg gtgtggaaag | 60 |
| tccccaggct ccccagcagg cagaagtatg caaagcatgc atctcaatta gtcagcaacc | 120 |
| aggtgtggaa agtccccagg ctccccagca ggcagaagta tgcaaagcat gcatctcaat | 180 |
| tagtcagcaa ccatagtccc gcccctaact ccgcccatcc cgcccctaac tccgcccagt | 240 |
| tccgcccatt ctccgcccca tggctgacta attttttta tttatgcaga ggccgaggcc | 300 |
| gcctcggcct ctgagctatt ccagaagtag tgaggaggct ttttggagg cctaggcttt | 360 |
| tgcaaaaagc tggatcgatc ctgagaactt cagggtgagt ttgggaccc ttgattgttc | 420 |
| tttcttttc gctattgtaa aattcatgtt atatggaggg ggcaaagttt tcagggtgtt | 480 |

```
gtttagaatg ggaagatgtc ccttgtatca ccatggaccc tcatgataat tttgtttctt    540
tcactttcta ctctgttgac aaccattgtc tcctcttatt ttcttttcat tttctgtaac    600
tttttcgtta aactttagct tgcatttgta acgaattttt aaattcactt ttgtttattt    660
gtcagattgt aagtactttc tctaatcact ttttttcaa ggcaatcagg gtatattata     720
ttgtacttca gcacagtttt agagaacaat tgttataatt aaatgataag gtagaatatt    780
tctgcatata aattctggct ggcgtggaaa tattcttatt ggtagaaaca actacatcct    840
ggtcatcatc ctgcctttct ctttatggtt acaatgatat acactgtttg agatgaggat    900
aaaatactct gagtccaaac cgggcccctc tgctaaccat gttcatgcct tcttcttttt    960
cctacagctc ctgggcaacg tgctggttat tgtgctgtct catcattttg gcaaagaatt   1020
gtaatacgac tcactatagg gcgaattcag gttctgtgga caatcacaat gggaatccaa   1080
ggagggtctg tcctgttcgg gctgctgctc gtcctggctg tcttctgcca ttcaggtcat   1140
agcctgcaga gctacaaccc tccgcgtacg gactacaagg acgatgatga caaacagatc   1200
agcggtggag gctcagaagt gggagaagac agcctgtcct tcaggcaagaa ggcccgcgag   1260
atagacgaga gcctcatctt ctacaagaag tgggagctgg aagcctgcgt ggatgcggcc   1320
ctgctggcca cccagatgga ccgcgtgaac gccatcccct tcacctacga gcagctggac   1380
gtcctaaagc ataaactgga tgagctctac ccacaaggtt accccgagtc tgtgatccag   1440
cacctgggct acctcttcct caagatgagc cctgaggaca ttcgcaagtg gaatgtgacg   1500
tccctggaga ccctgaaggc tttgcttgaa gtcaacaaag ggcacgaaat gagtcctcag   1560
gtggccaccc tgatcgaccg ctttgtgaag gaaggggcc agctagacaa agacacccta   1620
gacaccctga ccgccttcta ccctgggtac ctgtgctccc tcagccccga ggagctgagc   1680
tccgtgcccc ccagcagcat ctgggcggtc aggccccagg acctgacac gtgtgaccca   1740
aggcagctgg acgtcctcta tcccaaggcc cgccttgctt ccagaacat gaacgggtcc   1800
gaatacttcg tgaagatcca gtccttcctg ggtggggccc ccacggagga tttgaaggcg   1860
ctcagtcagc agaatgtgag catggacttg ccacgttca tgaagctgcg gacggatgcg   1920
gtgctgccgt tgactgtggc tgaggtgcag aaacttctgg accccacgt ggagggcctg   1980
aaggcggagg agcggcaccg cccggtgcgg gactggatcc tacggcagcg gcaggacgac   2040
ctggacacgc tggggctggg gctacagggc ctgcgtacgc cacctatgat tttgagaacc   2100
tctgaggaaa ccatttctac agttcaagaa aagcaacaaa atatttctcc cctagtgaga   2160
gaaagaggtc ctcagagagt agcagctcac ataactggga ccagaggaag aagcaacaca   2220
ttgtcttctc caaactccaa gaatgaaaag gctctgggcc gcaaaataaaa ctcctgggaa   2280
tcatcaagga gtgggcattc attcctgagc aacttgcact tgaggaatgg tgaactggtc   2340
atccatgaaa aagggtttta ctacatctat tcccaaacat actttcgatt tcaggaggaa   2400
ataaagaaa acacaaagaa cgacaaacaa atggtccaat atatttacaa atacacaagt   2460
tatcctgacc ctatattgtt gatgaaaagt gctagaaata gttgttggtc taaagatgca   2520
gaatatggac tctattccat ctatcaaggg ggaatatttg agcttaagga aaatgacaga   2580
atttttgttt ctgtaacaaa tgagcacttg atagacatgg accatgaagc cagttttttc   2640
ggggcctttt tagttggcag atcccaaaat atttctcccc tagtgagaga aagaggtcct   2700
cagagagtag cagctcacat aactgggacc agaggaagaa gcaacacatt gtcttctcca   2760
aactccaaga atgaaaaggc tctgggccgc aaaataaact cctgggaatc atcaaggagt   2820
gggcattcat tcctgagcaa cttgcacttg aggaatggtg aactggtcat ccatgaaaaa   2880
```

```
gggtttttact acatctattc ccaaacatac tttcgatttc aggaggaaat aaagaaaac    2940
acaaagaacg acaaacaaat ggtccaatat atttacaaat acacaagtta tcctgaccct    3000
atattgttga tgaaaagtgc tagaaatagt tgttggtcta aagatgcaga atatggactc    3060
tattccatct atcaaggggg aatatttgag cttaaggaaa atgacagaat ttttgtttct    3120
gtaacaaatg agcacttgat agacatggac catgaagcca gttttttcgg ggccttttta    3180
gttggcagat cccaccacca ccaccaccac caaaatattt ctcccctagt gagagaaaga    3240
ggtcctcaga gagtagcagc tcacataact gggaccagag aagaagcaa cacattgtct     3300
tctccaaact ccaagaatga aaaggctctg ggccgcaaaa taaactcctg gaatcatca     3360
aggagtgggc attcattcct gagcaacttg cacttgagga atggtgaact ggtcatccat    3420
gaaaaagggt tttactacat ctattcccaa acatactttc gatttcagga ggaaataaaa    3480
gaaaacacaa agaacgacaa acaaatggtc caatatattt acaaatacac aagttatcct    3540
gaccctatat tgttgatgaa aagtgctaga aatagttgtt ggtctaaaga tgcagaatat    3600
ggactctatt ccatctatca aggggaata tttgagctta aggaaaatga cagaattttt     3660
gtttctgtaa caaatgagca cttgatagac atggaccatg aagccagttt tttcggggcc    3720
ttttagttg gcagatctta atctaggatc ttattaaagc agaacttgtt tattgcagct    3780
tataatggtt acaaataaag caatagcatc acaaatttca caaataaagc attttttca    3840
ctgcattcta gttgtggttt gtccaaactc atcaatgtat cttatcatgt ctggtcgact    3900
ctagactctt ccgcttcctc gctcactgac tcgctgcgct cggtcgttcg ctgcggcga    3960
gcggtatcag ctcactcaaa ggcggtaata cggttatcca cagaatcagg ggataacgca    4020
ggaaagaaca tgtgagcaaa aggccagcaa aaggccagga accgtaaaaa ggccgcgttg    4080
ctggcgtttt tccataggct ccgccccct gacgagcatc acaaaaatcg acgctcaagt     4140
cagaggtggc gaaacccgac aggactataa agataccagg cgtttccccc tggaagctcc    4200
ctcgtgcgct ctcctgttcc gaccctgccg cttaccggat acctgtccgc ctttctccct    4260
tcgggaagcg tggcgctttc tcaatgctca cgctgtaggt atctcagttc ggtgtaggtc    4320
gttcgctcca agctgggctg tgtgcacgaa ccccccgttc agcccgaccg ctgcgcctta    4380
tccggtaact atcgtcttga gtccaacccg gtaagacacg acttatcgcc actggcagca    4440
gccactggta acaggattag cagagcgagg tatgtaggcg gtgctacaga gttcttgaag    4500
tggtggccta actacggcta cactagaagg acagtatttg gtatctgcgc tctgctgaag    4560
ccagttacct tcggaaaaag agttggtagc tcttgatccg gcaaacaaac caccgctggt    4620
agcggtggtt ttttttgtttg caagcagcag attacgcgca gaaaaaaagg atctcaagaa    4680
gatcctttga tctttctac ggggtctgac gctcagtgga acgaaaactc acgttaaggg     4740
attttggtca tgagattatc aaaaaggatc ttcacctaga tccttttaaa ttaaaaatga    4800
agttttaaat caatctaaag tatatatgag taaacttggt ctgacagtta ccaatgctta    4860
atcagtgagg cacctatctc agcgatctgt ctatttcgtt catccatagt tgcctgactc    4920
cccgtcgtgt agataactac gatacgggag ggcttaccat ctggccccag tgctgcaatg    4980
ataccgcgag acccacgctc accggctcca gatttatcag caataaacca gccagccgga    5040
agggccgagc gcagaagtgg tcctgcaact ttatccgcct ccatccagtc tattaattgt    5100
tgccgggaag ctagagtaag tagttcgcca gttaatagtt tgcgcaacgt tgttgccatt    5160
gctacaggca tcgtggtgtc acgctcgtcg tttggtatgg cttcattcag ctccggttcc    5220
caacgatcaa ggcgagttac atgatccccc atgttgtgca aaaaagcggt tagctccttc    5280
```

```
ggtcctccga tcgttgtcag aagtaagttg gccgcagtgt tatcactcat ggttatggca    5340
gcactgcata attctcttac tgtcatgcca tccgtaagat gcttttctgt gactggtgag    5400
tactcaacca agtcattctg agaatagtgt atgcggcgac cgagttgctc ttgcccggcg    5460
tcaatacggg ataataccgc gccacatagc agaactttaa aagtgctcat cattggaaaa    5520
cgttcttcgg ggcgaaaact ctcaaggatc ttaccgctgt tgagatccag ttcgatgtaa    5580
cccactcgtg cacccaactg atcttcagca tcttttactt tcaccagcgt ttctgggtga    5640
gcaaaaacag gaaggcaaaa tgccgcaaaa aagggaataa gggcgacacg gaaatgttga    5700
atactcatac tcttcttttt tcaatattat tgaagcattt atcagggtta ttgtctcatg    5760
agcggataca tatttgaatg tatttagaaa aataaacaaa taggggttcc gcgcacattt    5820
ccccgaaaag tgccacctga cgtctaagaa accattatta tcatgacatt aacctataaa    5880
aataggcgta tcacgaggcc cctttcgtct cgcgcgtttc ggtgatgacg gtgaaaacct    5940
ctgacacatg cagctcccgg agacggtcac agcttgtctg taagcggatg ccggagcag    6000 acaagcccgt cagggcgcgt cagcgggtgt tggcgggtgt cggggctggc ttaactatgc    6060
ggcatcagag cagattgtac tgagagtgca ccatatgcgg tgtgaaatac cgcacagatg    6120
cgtaaggaga aaataccgca tcaggaaatt gtaaacgtta atattttgtt aaaattcgcg    6180
ttaaattttt gttaaatcag ctcattttt aaccaatagg ccgaaatcgg caaaatccct    6240
tataaatcaa agaatagac cgagataggg ttgagtgttg ttccagtttg gaacaagagt    6300
ccactattaa agaacgtgga ctccaacgtc aaagggcgaa aaaccgtcta tcagggcgat    6360
ggcccactac gtgaaccatc acctaatca gttttttgg ggtcgaggtg ccgtaaagca    6420
ctaaatcgga accctaaagg gagcccccga tttagagctt gacggggaaa gccggcgaac    6480
gtggcgagaa aggaagggaa gaaagcgaaa ggagcgggcg ctagggcgct ggcaagtgta    6540
gcggtcacgc tgcgcgtaac caccacaccc gccgcgctta atgcgccgct acagggcgcg    6600
tcgcgccatt cgccattcag gctacgcaac tgttgggaag ggcgatcggt gcgggcctct    6660
tcgctattac gccagctggc gaagggggga tgtgctgcaa ggcgattaag ttgggtaacg    6720
ccagggtttt cccagtcacg acgttgtaaa acgacggcca gtgaatt              6767
```

<210> SEQ ID NO 4
<211> LENGTH: 5858
<212> TYPE: DNA
<213> ORGANISM: artificial
<220> FEATURE:
<223> OTHER INFORMATION: plasmid encoding fusion polypeptide

<400> SEQUENCE: 4

```
gtcgacttct gaggcggaaa gaaccagctg tggaatgtgt gtcagttagg gtgtggaaag      60
tccccaggct ccccagcagg cagaagtatg caaagcatgc atctcaatta gtcagcaacc     120
aggtgtggaa agtccccagg ctccccagca ggcagaagta tgcaaagcat gcatctcaat     180
tagtcagcaa ccatagtccc gcccctaact ccgcccatcc cgcccctaac tccgcccagt     240
tccgcccatt ctccgcccca tggctgacta atttttttta tttatgcaga ggccgaggcc     300
gcctcggcct ctgagctatt ccagaagtag tgaggaggct tttttggagg cctaggcttt     360
tgcaaaaagc tggatcgatc ctgagaactt cagggtgagt ttggggaccc ttgattgttc     420
tttctttttc gctattgtaa aattcatgtt atatggaggg gcaaagtttt cagggtgtt     480 gtttagaatg ggaagatgtc ccttgtatca ccatggaccc tcatgataat tttgtttctt     540
tcactttcta ctctgttgac aaccattgtc tcctcttatt ttcttttcat ttctgtaac     600
```

```
tttttcgtta aactttagct tgcatttgta acgaattttt aaattcactt ttgtttattt      660
gtcagattgt aagtactttc tctaatcact ttttttttcaa ggcaatcagg gtatattata    720
ttgtacttca gcacagtttt agagaacaat tgttataatt aaatgataag gtagaatatt    780
tctgcatata aattctggct ggcgtggaaa tattcttatt ggtagaaaca actacatcct    840
ggtcatcatc ctgcctttct ctttatggtt acaatgatat acactgtttg agatgaggat    900
aaaatactct gagtccaaac cgggcccctc tgctaaccat gttcatgcct tcttcttttt    960
cctacagctc ctgggcaacg tgctggttat tgtgctgtct catcattttg gcaaagaatt    1020
gtaatacgac tcactatagg gcgaattcag gttctgtgga caatcacaat gggaatccaa    1080
ggagggtctg tcctgttcgg gctgctgctc gtcctggctg tcttctgcca ttcaggtcat    1140
agcctgcaga gctacaaccc ccgcgtacg ccacctatga ttttgagaac ctctgaggaa    1200
accatttcta cagttcaaga aaagcaacaa aatatttctc ccctagtgag agaaagaggt    1260
cctcagagag tagcagctca cataactggg accagaggaa gaagcaacac attgtcttct    1320
ccaaactcca agaatgaaaa ggctctgggc cgcaaaataa actcctggga atcatcaagg    1380
agtgggcatt cattcctgag caacttgcac ttgaggaatg gtgaactggt catccatgaa    1440 aaagggttttt actacatcta ttcccaaaca tactttcgat tcaggagga aataaaagaa    1500 aacacaaaga acgacaaaca aatggtccaa tatatttaca aatacacaag ttatcctgac    1560
cctatattgt tgatgaaaag tgctagaaat agttgttggt ctaaagatgc agaatatgga    1620
ctctattcca tctatcaagg gggaatattt gagcttaagg aaaatgacag aattttttgtt    1680 tctgtaacaa atgagcactt gatagacatg gaccatgaag ccagttttttt cggggccttt    1740 ttagttggca gatcccaaaa tatttctccc ctagtgagag aaagaggtcc tcagagagta    1800
gcagctcaca taactgggac cagaggaaga agcaacacat gtcttctcc aaactccaag    1860 aatgaaaagg ctctgggccg caaaataaac tcctgggaat catcaaggag tgggcattca    1920
ttcctgagca acttgcactt gaggaatggt gaactggtca tccatgaaaa agggttttac    1980
tacatctatt cccaaacata ctttcgattt caggaggaaa taaagaaaa cacaaagaac    2040 gacaaacaaa tggtccaata tatttacaaa tacacaagtt atcctgaccc tatattgttg    2100
atgaaaagtg ctagaaatag ttgttggtct aaagatgcag aatatggact ctattccatc    2160
tatcaagggg gaatatttga gcttaaggaa aatgacagaa tttttgtttc tgtaacaaat    2220
gagcacttga tagacatgga ccatgaagcc agttttttcg ggcctttttt agttggcaga    2280
tcccaccacc accaccacca ccaaaatatt tctcccctag tgagagaaag aggtcctcag    2340
agagtagcag ctcacataac tgggaccaga ggaagaagca acacattgtc ttctccaaac    2400
tccaagaatg aaaaggctct gggccgcaaa ataaactcct gggaatcatc aaggagtggg    2460
cattcattcc tgagcaactt gcacttgagg aatggtgaac tggtcatcca tgaaaaaggg    2520
ttttactaca tctattccca acatactttt cgatttcagg aggaaataaa agaaaacaca    2580
aagaacgaca aacaaatggt ccaatatatt tacaaataca aagttatcc tgaccctata    2640 ttgttgatga aaagtgctag aaatagttgt tggtctaaag atgcagaata tggactctat    2700
tccatctatc aagggggaat atttgagctt aaggaaaatg acagaatttt tgtttctgta    2760
acaaatgagc acttgataga catggaccat gaagccagtt ttttcggggc ttttttagtt    2820
ggcagatctt aatctaggat cttattaaag cagaacttgt ttattgcagc ttataatggt    2880
tacaaataaa gcaatagcat cacaaatttc acaaataaag catttttttc actgcattct    2940
agttgtggtt tgtccaaact catcaatgta tcttatcatg tctggtcgac tctagactct    3000
```

```
tccgcttcct cgctcactga ctcgctgcgc tcggtcgttc ggctgcggcg agcggtatca    3060
gctcactcaa aggcggtaat acggttatcc acagaatcag gggataacgc aggaaagaac    3120
atgtgagcaa aaggccagca aaaggccagg aaccgtaaaa aggccgcgtt gctggcgttt    3180
ttccataggc tccgcccccc tgacgagcat cacaaaaatc gacgctcaag tcagaggtgg    3240
cgaaacccga caggactata aagataccag gcgtttcccc ctggaagctc cctcgtgcgc    3300
tctcctgttc cgaccctgcc gcttaccgga tacctgtccg cctttctccc ttcgggaagc    3360
gtggcgcttt ctcaatgctc acgctgtagg tatctcagtt cggtgtaggt cgttcgctcc    3420
aagctgggct gtgtgcacga accccccgtt cagcccgacc gctgcgcctt atccggtaac    3480
tatcgtcttg agtccaaccc ggtaagacac gacttatcgc cactggcagc agccactggt    3540
aacaggatta gcagagcgag gtatgtaggc ggtgctacag agttcttgaa gtggtggcct    3600
aactacggct acactagaag gacagtattt ggtatctgcg ctctgctgaa gccagttacc    3660
ttcggaaaaa gagttggtag ctcttgatcc ggcaaacaaa ccaccgctgg tagcggtggt    3720
ttttttgttt gcaagcagca gattacgcgc agaaaaaaag gatctcaaga agatcctttg    3780
atcttttcta cggggtctga cgctcagtgg aacgaaaact cacgttaagg gattttggtc    3840
atgagattat caaaaaggat cttcacctag atccttttaa attaaaaatg aagttttaaa    3900
tcaatctaaa gtatatatga gtaaacttgg tctgacagtt accaatgctt aatcagtgag    3960
gcacctatct cagcgatctg tctatttcgt tcatccatag ttgcctgact ccccgtcgtg    4020
tagataacta cgatacggga gggcttacca tctggcccca gtgctgcaat gataccgcga    4080
gacccacgct caccggctcc agatttatca gcaataaacc agccagccgg aagggccgag    4140
cgcagaagtg gtcctgcaac tttatccgcc tccatccagt ctattaattg ttgccgggaa    4200
gctagagtaa gtagttcgcc agttaatagt ttgcgcaacg ttgttgccat tgctacaggc    4260
atcgtggtgt cacgctcgtc gtttggtatg gcttcattca gctccggttc ccaacgatca    4320
aggcgagtta catgatcccc catgttgtgc aaaaaagcgg ttagctcctt cggtcctccg    4380
atcgttgtca gaagtaagtt ggccgcagtg ttatcactca tggttatggc agcactgcat    4440
aattctctta ctgtcatgcc atccgtaaga tgcttttctg tgactggtga gtactcaacc    4500
aagtcattct gagaatagtg tatgcggcga ccgagttgct cttgcccggc gtcaatacgg    4560
gataataccg cgccacatag cagaacttta aaagtgctca tcattggaaa acgttcttcg    4620
gggcgaaaac tctcaaggat cttaccgctg ttgagatcca gttcgatgta acccactcgt    4680
gcacccaact gatcttcagc atcttttact ttcaccagcg tttctgggtg agcaaaaaca    4740
ggaaggcaaa atgccgcaaa aaagggaata agggcgacac ggaaatgttg aatactcata    4800
ctcttccttt ttcaatatta ttgaagcatt tatcagggtt attgtctcat gagcggatac    4860
atatttgaat gtatttagaa aaataaacaa ataggggttc cgcgcacatt tccccgaaaa    4920
gtgccacctg acgtctaaga aaccattatt atcatgacat taacctataa aaataggcgt    4980
atcacgaggc cctttcgtc tcgcgcgttt cggtgatgac ggtgaaaacc tctgacacat    5040
gcagctcccg gagacggtca cagcttgtct gtaagcggat gccgggagca gacaagcccg    5100
tcagggcgcg tcagcgggtg ttggcgggtg tcggggctgg cttaactatg cggcatcaga    5160
gcagattgta ctgagagtgc accatatgcg gtgtgaaata ccgcacagat gcgtaaggag    5220
aaaataccgc atcaggaaat tgtaaacgtt aatattttgt taaaattcgc gttaaatttt    5280
tgttaaatca gctcattttt taaccaatag gccgaaatcg gcaaaatccc ttataaatca    5340
aaagaataga ccgagatagg gttgagtgtt gttccagttt ggaacaagag tccactatta    5400
```

```
aagaacgtgg actccaacgt caaagggcga aaaaccgtct atcagggcga tggcccacta    5460
cgtgaaccat caccctaatc aagtttttg gggtcgaggt gccgtaaagc actaaatcgg     5520
aaccctaaag ggagcccccg atttagagct tgacggggaa agccggcgaa cgtggcgaga    5580
aaggaaggga agaaagcgaa aggagcgggc gctagggcgc tggcaagtgt agcggtcacg    5640
ctgcgcgtaa ccaccacacc cgccgcgctt aatgcgccgc tacagggcgc gtcgcgccat    5700
tcgccattca ggctacgcaa ctgttgggaa gggcgatcgg tgcgggcctc ttcgctatta    5760
cgccagctgg cgaagggggg atgtgctgca aggcgattaa gttgggtaac gccagggttt    5820
tcccagtcac gacgttgtaa aacgacggcc agtgaatt                            5858
```

TUMOR TARGETED TNF-RELATED APOPTOSIS INDUCING LIGAND FUSION POLYPEPTIDE, METHODS AND USES THEREFOR

CROSS-REFERENCE TO RELATED APPLICATION

This application is a Continuation of, and claims benefit of priority to U.S. Non-Provisional application Ser. No. 13/892,238, filed May 10, 2013. Application Ser. No. 13/892,238 claims the benefit of U.S. Provisional Patent Application 61/645,058 filed May 10, 2012. These applications are incorporated by reference, each in its entirety.

STATEMENT REGARDING FEDERALLY SPONSORED RESEARCH OR DEVELOPMENT

This invention was made with government support under Grants TR000448 and CA150945 awarded by the National Institutes of Health. The Government has certain rights in the invention.

INCORPORATION BY REFERENCE OF SEQUENCE LISTING

The Sequence Listing, which is a part of the present disclosure, includes a computer readable form and a written sequence listing comprising nucleotide and/or amino acid sequences. The sequence listing information recorded in computer readable form is identical to the written sequence listing. The subject matter of the Sequence Listing is incorporated herein by reference in its entirety.

INTRODUCTION

Pancreatic cancer is among those malignancies with the worst prognoses in the United States in 2010 (Jemal, A., et al. CA Cancer J. Clin. 60:277-300, 2010). There has been little progress in the management of the disease and the annual mortality rate remains nearly identical to the annual incidence rate. The five-year survival for pancreatic cancer patients is ~4%.

Transformed cancer cells can often be distinguished from normal tissues by changes in expression patterns of certain cellular markers. Two cell surface antigens with expression levels that can exceed normal levels in cancer cells are mesothelin and MUC16 (also known as CA-125).

Mesothelin is a GPI-linked cell surface glycoprotein that is believed to participate in tumor adhesion and dissemination including formation of metastases (Hassan, R., et al. Clin. Cancer Res. 10:3937-42, 2004). Mesothelin is expressed in mesothelial cells with limited expression in other normal cell types. Expression of mesothelin can be substantially up-regulated in human pancreas and ovarian cancers. For example, analyses of human pancreas cancers have shown greater than 3 fold up-regulation of mesothelin gene expression (Iacobuzio-Donahue, C. A., et al. Cancer Res. 63:8614-22, 2003). In one study, mesothelin expression was identified in pancreas adenocarcinomas (the far majority of pancreas cancers are ductal adenocarcinomas, PDACs) in all 60 patients examined by immunohistochemistry (Argani, P., et al. Clin. Cancer Res. 7:3862-8, 2001). In addition, mesothelin overexpression is commonly found in ovarian malignancies, lung cancer, and mesotheliomas (Ho, M., et al. Clin. Cancer Res. 13:1571-5, 2007; Muminova, Z. E., et al. BMC Cancer. 4:19, 2004; Ho, M., et al. Clin. Cancer Res. 11:3814-20, 2005). In addition, there is evidence that over-expression of mesothelin may be essential for progression of pancreas cancer, (Li, M., et al. Mol. Cancer Ther. 7:286-96, 2008). It has been shown that the N-terminal 64 amino acid sequence of mesothelin includes the minimal binding sequence required for MUC16 binding (Xiang, X., et al., J. Cancer 2: 280-291, 2011).

MUC16 (CA125) belongs to a group of mucins expressed on epithelial cells (Kufe, D. W. Nat. Rev. Cancer. 9:874-85, 2009). MUC16 is transmembrane anchored. In addition, patients with pancreatic cancer can have serum MUC16 levels that can be nearly 40-fold increased compared to healthy controls or patients with benign pancreatic lesions (Brand, R. E., et al. Clin. Cancer Res. 17:805-16, 2011). Membrane-bound MUC16 binds to native mesothelin with high affinity, whereas soluble MUC16 has only a weak affinity for mesothelin (Rump, A., et al. J. Biol. Chem. 279:9190-8, 2004; Bast, R. C., et al. Int. J. Gynecol. Cancer. 15:274-81, 2005; Gubbels, J. A., et al. Mol. Cancer. 5:50, 2006).

TNF-related apoptosis-inducing ligand (TRAIL) has been shown to exhibit potent apoptotic activity against tumor cells with lower toxicity to non-transformed cells following engagement with cellular receptors expressed abundantly on tumor cells (Falschlehner, C., et al. J. Biochem. Cell Bio. 39:1462-1475, 2007). TRAIL stimulates the extrinsic death pathway. Native, soluble TRAIL exists as a homotrimer in vivo (Kohlhaas, S. L., et al. J. Biol. Chem. 282: 12831-12841, 2007). The sequence of human TRAIL amino acids 91-281 is:

```
                                           (SEQ ID NO: 1)
MILRTSEETISTVQEKQQNISPLVRERGPQRVAAHITGTRGRSNTLSSP

NSKENKALGRKINSWESSRSGHSFLSNLHLRNGELVIHEKGFYYIYSQT

YFRFQEEIKENTKNKDQMVQYIYKYTSYPDPILLMKSARNSCWSKDAEY

GLYSIYQGGIFELKENDRIFVSVTNEHLIDMDHEASFFGAFLVG.
```

Recombinant TRAIL has been produced in bacteria exclusively from monomeric cDNAs. However, the activity of recombinant TRAIL depends on trimerization (Spitzer, D., et al., Mol. Cancer Ther. 9: 2142-2151, 2010). Numerous design modifications have been used to generate molecules comprising trimerized TRAIL sequences, such as: tagging with FLAG sequence or His-tagging, with tag-mediated crosslinking; addition of leucine zipper [LZ] and/or isoleucine zipper [ILZ] sequences, with stabilization of TR3 trimers with cations [i.e., zinc] (Merino, D., et al. Expert Opin. Ther. Targets. 11: 1299-1314, 2007). However, such attempts to produce bioactive TRAIL from monomeric cDNAs in mammalian cells have failed. Such failures have been attributed to intermolecular disulfide bridge formation via TRAIL's unique cysteine at amino acid 230, resulting in a non-functional death receptor ligand (Bodmer, J. L., et al., J.Biol. Chem. 275: 20632-20637, 2000).

Previously, the present inventors developed bioactive TRAIL trimers ("TR3") (U.S. patent application Ser. No. 13/155,577, published as US Patent Application Publication 2011/0300629 A1; Spitzer, D., et al., Mol. Cancer Ther. 9: 2142-2151, 2010). Furthermore, the present inventors also developed numerous modifications to further enhance TR3's pharmacologic properties over conventional TRAIL, including enhanced temperature stability and prolonged in vivo half-life (Spitzer, D., et al. Mol. Cancer Ther. 9:2142-51, 2010).

However, there is an unmet need for therapeutically active compositions that can induce cell death in tumor cell targets.

SUMMARY

In view of the unmet need for therapeutically effective reagents that target and cause death of tumor cells while minimizing toxicity to non-cancerous cells, the present inventors disclose fusion polypeptides comprising TRAIL trimers and targeting domains, and nucleic acids comprising sequences encoding such fusion polypeptides. In various embodiments, a fusion polypeptide of the present teachings can comprise, consist essentially of, or consist of a sequence of a TRAIL trimer plus a polypeptide sequence that can target a tumor cell such as, for example, a tumor cell that expresses abnormally high levels of a cell surface receptor such as MUC16. In various embodiments, a fusion polypeptide of the present teachings can comprise, consist essentially of, or consist of a sequence of a TRAIL trimer and a polypeptide sequence that can target a TRAIL trimer to a tumor cell such as, for example and without limitation, a pancreatic tumor cell or an ovarian cancer cell. In various embodiments, a fusion polypeptide of the present teachings can comprise, consist essentially of, or consist of a sequence of a TRAIL trimer plus a targeting sequence such as a mesothelin polypeptide. In various embodiments, the sequence of a mesothelin polypeptide can be that of a full length mesothelin, or a mesothelin of less than full length but retains MUC16 binding activity. In various embodiments, a fusion polypeptide of the present teachings can comprise, consist essentially of, or consist of a TRAIL trimer sequence plus a mesothelin sequence absent the GPI anchor. In various embodiments, a fusion polypeptide of the present teachings can comprise, consist essentially of, or consist of a TRAIL trimer sequence plus an N-terminal peptide sequence of mesothelin, such as, without limitation, the 64 amino acid sequence of the N-terminal of human mesothelin. In various embodiments, a fusion polypeptide of the present teachings can further comprise one or more linker sequences such as described in U.S. patent application Ser. No. 13/155,577 filed Jun. 8, 2011, published as US Patent Application Publication 2011/0300629 A1, and Spitzer, D., et al., Mol. Cancer Ther. 9: 2142-2151, 2010 which are hereby incorporated by reference, each in its entirety. In some configurations, a spacer can comprise, consist essentially of, or consist of one or more short consensus repeats (SCRs). In various configurations, a spacer can comprise, consist essentially of, or consist of one SCR, two SCRs, three SCRs or four SCRs. In some configurations, a fusion polypeptide can further comprise a tag sequence, such as, without limitation, a 6-His tag sequence and/or a FLAG sequence.

In various embodiments, a fusion polypeptide of the present teachings can be selected from the group consisting of complete mesothelin-TR3 (i.e., a fusion polypeptide comprising full-length mesothelin, plus TR3); mesothelinΔGPI-TR3 (i.e., a fusion polypeptide comprising mesothelin consisting of GPI-anchor-deleted mesothelin, plus TR3) and meso64-TR3 (i.e., a fusion polypeptide comprising a mesothelin consisting of the N-terminal 64 amino acids of mesothelin, plus TR3).

In various embodiments, the present teachings further include nucleic acids that encode any of the fusion polypeptides disclosed herein, as well as vectors such as viruses and plasmids comprising a nucleic acid that encodes any of the fusion polypeptides disclosed herein.

In some embodiments, a fusion polypeptide of the present teachings does not activate cell death pathways when contacted with a MUC16-negative cell at a concentration at which a TRAIL trimer alone (i.e., without mesothelin) activates cell death pathways in a MUC16-negative cell.

In some embodiments, a fusion polypeptide of the present teachings can bind to the surface of cells expressing MUC16, such as, for example, pancreatic or ovarian tumor cells.

In some embodiments, a fusion polypeptide of the present teachings can induce apoptosis in cells that express MUC16 such as tumor cells that express MUC16.

In some embodiments, a fusion polypeptide of the present teachings can block native binding sites of MUC16 in cells expressing MUC16, such as, for example, pancreatic or ovarian tumor cells.

In some embodiments, a fusion polypeptide of the present teachings can reduce metastatic potential of tumor cells that express MUC16.

Various embodiments of the present teachings include methods of treating cancer. In various configurations, these methods comprise administering to a subject in need thereof a therapeutically effective amount of a fusion polypeptide of the present teachings. In various configurations, the methods comprise administering to a subject in need thereof a therapeutically effective amount of a vector such as a plasmid or virus comprising a nucleic acid encoding a fusion polypeptide of the present teachings.

In various embodiments, methods of the present teachings include methods of inducing apoptosis in a cell that expresses MUC16 such as a tumor cell that expresses MUC16. In various configurations, these methods include contacting a cell that expresses MUC16 with a polypeptide of the present teachings, or a nucleic acid or vector of the present teachings. In various configurations, a fusion polypeptide or nucleic acid can be administered in an amount sufficient to cause apoptosis in a cell that expresses MUC16 without inducing apoptosis in other cells.

In various embodiments, methods of the present teachings include methods of blocking native binding sites of MUC16. In these methods, a fusion polypeptide of the present teachings or a nucleic acid encoding a fusion polypeptide of the present teachings is administered or applied to a cell expressing MUC16.

In various embodiments, methods of the present teachings include methods of reducing metastatic potential. In these methods, a fusion polypeptide of the present teachings or a nucleic acid encoding a fusion polypeptide of the present teachings is administered or applied to a cell expressing MUC16.

In various embodiments, methods of the present teachings include methods of killing MUC16-positive cells in a population of cells. In various configurations, these methods comprise contacting the cells of a population of cells with an effective amount of a fusion polypeptide or a nucleic acid of the present teachings, whereby >70% of MUC16-positive cells are killed, i.e., at a percentage greater than a "chemotherapeutic plateau."

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4A-D illustrate Meso-TR3 binding to MUC16-expressing cancer targets.

FIG. 5A-E illustrate cell killing of MUC16-positive cells by a mesothelin-TR3 fusion polypeptide.

FIG. 14 illustrates production and killing potential of TR3, Meso64-TR3, and Meso-TR3.

DETAILED DESCRIPTION

Figure 1:
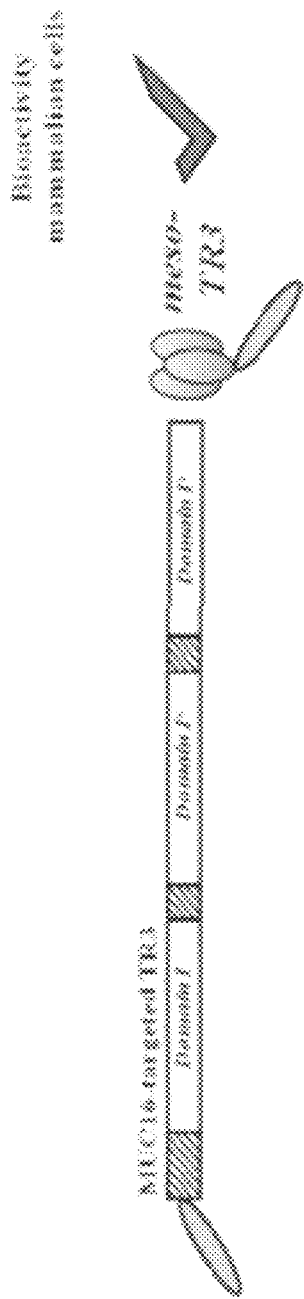
FIG. 1 illustrates a fusion polypeptide of the present teachings.

A desired feature of a therapeutic is that after systemic application, it seeks its target automatically, ignores all non-targets and, when arrived at its destination fully unleashes its intended pharmacologic activity, in analogy of a "magic bullet". Such a selective activity profile can be beneficial for the treatment of human malignancies, for example when treatment with conventional chemotherapy is known to be associated with debilitating side effects directly linked to an adverse impact on the quality of life of the patients.

Nearly 20 years ago, the TNF superfamily member TRAIL was identified as a potential cancer therapeutic because of its strong apoptosis induction on transformed cancer cells and lack of harmful side effects for the host. Since then, TRAIL has been evaluated in a number of clinical trials and found to be effective against several types of cancers (Herbst, R. S., et al., J. Clin. Oncol. 28:2839, 2010). Investigators have looked for ways to stabilize the bioactive trimer by a number of attempts, such as adding Zn2+ to the production process which is believed to aid the coordination of the free cysteines (Mahalingam, D., et al., Cancer Treat. Rev. 35:280, 2009). Incorporation of targeting moieties directed against cancer-specific surface markers was also investigated. In these studies, cancer targeting was primarily achieved using antibody fragments (scFv) on the basis of the conventional monomeric TRAIL platform (Bremer, E., et al., Int. J. Cancer 109:281, 2004, ten Cate, B., et al., Leukemia 23:1389, 2009). This technology turned out to be quite effective, despite a 1:1 stoichiometry of the targeting and effector domain of the fusion proteins which could potentially interfere with the formation of bioactive TRAIL trimers, resulting in unpredictable drug properties. In fact, we have produced scFv-TRAIL fusion proteins employing two different antibody fragments with one drug being constitutively active while the other drug was completely inactive in the absence of the target antigen.

The present inventors have recently designed a new method to produce bioactive soluble TRAIL from mammalian cells, designated TR3. Despite its much enhanced stability, this genetically fused TRAIL trimer has the capacity to serve as a drug platform for the design of targeted TRAIL therapy under stoichiometric control. This has been shown by fusing a scFv to the N-terminus of TR3 which resulted in a RBC-targeted scFv-TR3 fusion protein with a favorable 1:3 stoichiometry that was capable of tethering human TR3 to mouse RBCs which were converted into potent effector surfaces in analogy to nanoparticles, only capable of facilitating bystander killing (Spitzer, D., et al., Mol. Cancer Ther. 9:2142, 2010). In the instant application, we have described the in vitro characterization of a tumor-targeted variant of TR3 by harnessing the strong binding affinity of the two well described biomarkers mesothelin and MUC16. Instead of targeting TR3 via an antibody fragment to the desired cancer cells, the present inventors generated Meso-TR3, in which the mature form of secreted human mesothelin was placed at the N-terminus of human TR3. Meso-TR3 bound abundantly to endogenous MUC16, identical to soluble mesothelin itself and triggered a much enhanced death pathway than the parental drug TR3. These results had important implications because they confirmed that the mesothelin targeting domain was not masked by TR3 as it was still accessible to interact with membrane-associated MUC16. This interaction is important because it not only imparts target selectivity to Meso-TR3, but also serves to anchor soluble TRAIL to the surface of MUC16-positive cancer cells, thus converting it into a membrane bound TRAIL.

This conversion has been proposed to lead a more efficient receptor crosslinking (particularly important for DR5-mediated apoptosis), which in turn provides a more potent death signal resulting in an enhanced apoptosis compared to its soluble counterpart (Muhlenbeck, F., et al., J. Biol. Chem. 275:32208, 2000).

Figure 7A:
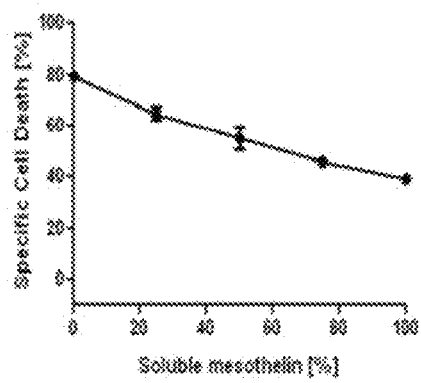
FIG. 7A-D illustrate phenotypic characterization of MUC16-targeted Meso-TR3.
Figure 7B:
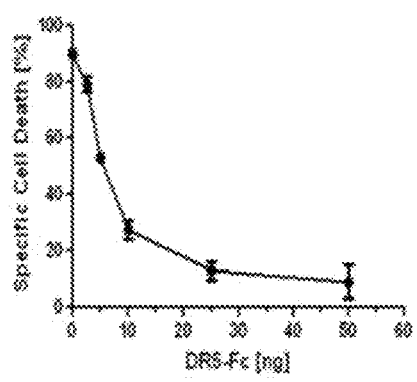
Figure 7C:
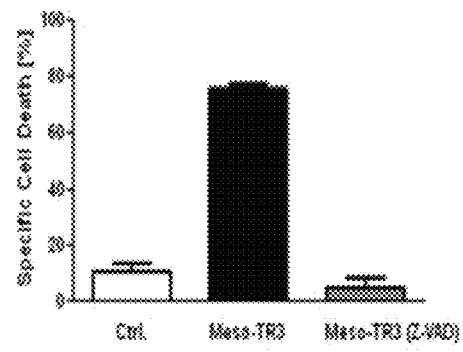
Figure 7D:
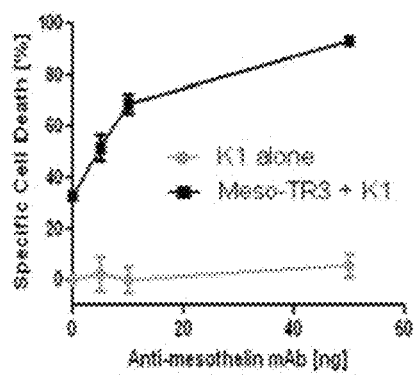

The importance of TRAIL receptor crosslinking in cell death is further exemplified by an enhanced induction of apoptosis noted in our experimental system upon adding mesothelin antibody to dimerize Meso-TR3, ultimately resulting in a more efficient TRAIL receptor crosslinking (FIG. 7D). Another potentially important aspect of the binding of mesothelin to MUC16 is that it may contribute to both homotypic (tumor cell-tumor cell) and heterotypic (tumor cell-mesothelial cell) cell interactions (Singh, A. P., et al., Cancer Res. 64:622, 2004). The latter type of cell interaction is believed to promote adherence of tumor cells to the peritoneum, resulting in metastatic spread of the primary lesion into the abdomen (Gubbels, J. A., et al., Mol. Cancer 5:50, 2006; Rump, A., J. Biol. Chem. 279:9190, 2004; Scholler, N., et al., Cancer Lett. 247:130, 2007). These considerations suggest that by virtue of binding to MUC16, Meso-TR3 may also block the mesothelin/MUC16-dependent cell adhesion thus limiting the peritoneal dissemination of tumor cells in addition to facilitating enhanced TRAIL-mediated target cell death (Bergan, L., Cancer Lett. 255:263, 2007).

While the TR3 effector domain of Meso-TR3 did not seem to sterically interfere with binding the drug to MUC16, we noticed potential limitations with regard to TR3 binding to the DR5 receptor on MUC16-deficient targets. Based on semi-quantitative Western blot analysis, an ≈8-fold higher concentration of Meso-TR3 was required to achieve the same biological effect as untargeted TR3 on MUC16-deficient Jurkat cells. This finding was somewhat inconsistent with our earlier report in which we did not observe detrimental effects on the killing activity of a variety of domain additions engineered onto the TR3 drug platform (Spitzer, D., et al., Mol. Cancer Ther. 9:2142, 2010). A possible explanation for this finding is that, in its native state, the steric relationship between mesothelin and TR3 in the context of the Meso-TR3 fusion protein might be such that it partially masks the TR3 molecule and makes it less accessible to the death receptors in target antigen negative cells (FIG. 9B, left panel). However, when the mesothelin targeting moiety is bound to MUC16, exposure of the TR3 trimer is enabled and results in an unrestricted accessibility with the surface-associated death receptor(s). We therefore propose that these structural changes, in combination with a now membrane tethered TR3 are responsible for Meso-TR3 to acquire its full cytotoxic potential at the target cell membrane (FIG. 9B, right panel).

In summary, the present inventors have described the in vitro characterization of a downstream modification of the novel TRAIL-based drug platform TR3. Soluble Meso-TR3 targets the cancer biomarker MUC16 and exhibits all features of a traditional TRAIL-based cancer drug, combined with enhanced stability, killing capacity and favorable 1:3 stoichiometry of targeting (mesothelin) and effector domain (TR3). Methods The methods and compositions described herein utilize laboratory techniques well known to skilled artisans, and can be found in references such as Sambrook and Russel (2006), Condensed Protocols from Molecular Cloning: A Laboratory Manual, Cold Spring Harbor Laboratory Press, ISBN 0879697717; Sambrook and Russel (2001) Molecular Cloning: A Laboratory Manual, Cold Spring Harbor Laboratory Press, ISBN 0879695773; Ausubel et al. (2002) Short Protocols in Molecular Biology, Current Protocols, ISBN 0471250929; Spector et al. (1998) Cells: A Laboratory Manual, Cold Spring Harbor Laboratory Press, ISBN 0879695226. As used herein, "TRAIL" can refer to full-length TRAIL polypeptide, or a domain thereof, such as TRAIL I domain (amino acids 91-113 human TRAIL) or TRAIL I' domain (amino acids 108-113 human TRAIL).

Non-limiting examples of fusion polypeptides of the present teachings include, in amino-terminal-to carboxy terminal order:

1. Mesothelin-TRAIL domain I-TRAIL domain I'-TRAIL domain I', wherein "mesothelin" is full-length human mesothelin; TRAIL domain I is human TRAIL fragment aa 91-113, TRAIL domain I' is human TRAIL fragment aa 108-113.
2. Mesothelin-TRAIL domain I-TRAIL domain I'-TRAIL domain I' wherein "mesothelin" is human mesothelin from which carboxy terminal sequence comprising the GPI anchor domain had been deleted; TRAIL domain I is human TRAIL fragment aa 91-113, TRAIL domain I' is human TRAIL fragment aa 108-113.
3. Mesothelin-TRAIL domain I-TRAIL domain I'-TRAIL domain I' wherein "mesothelin" consists of amino acids 1-64 of human mesothelin; TRAIL domain I is human TRAIL fragment aa 91-113, TRAIL domain I' is human TRAIL fragment aa 108-113.
4. Mesothelin-TRAIL domain I-TRAIL domain I'-TRAIL domain I' wherein "mesothelin" is a human mesothelin fragment that binds MUC16, such as without limitation amino acids 1-64; TRAIL domain I is human TRAIL fragment aa 91-113, TRAIL domain I' is human TRAIL fragment aa 108-113.

Vectors

Examples of vectors of the present teachings include, without limitation, plasmids of the following sequences.

```
p5FhMeso64TR3HIS2Q (6113 BP) (FIG. 10):
                                                       (SEQ ID NO: 2)
gtcgacttct gaggcggaaa gaaccagctg tggaatgtgt gtcagttagg gtgtggaaag    60
tccccaggct ccccagcagg cagaagtatg caaagcatgc atctcaatta gtcagcaacc   120
aggtgtggaa agtccccagg ctccccagca ggcagaagta tgcaaagcat gcatctcaat   180
tagtcagcaa ccatagtccc gcccctaact ccgcccatcc cgcccctaac tccgcccagt   240
tccgcccatt ctccgcccca tggctgacta atttttttta tttatgcaga ggccgaggcc   300
gcctcggccc ctgagctatt ccagaagtag tgaggaggct tttttggagg cctaggcttt   360
tgcaaaaagc tggatcgatc ctgagaactt cagggtgagt ttggggaccc ttgattgtcc   420
tttctttttc gctattgtaa aattcatgtt atatggaggg ggcaaagttt tcagggtgtt   480
gtttagaatg ggaagatgtc ccttgtatca ccatggaccc tcatgataat tttgtttctt   540
tcactctcta ctctgttgac aaccattgtc tcctcttatt ctcttttcat tttctgtaac   600
tttttcgtta aactttagct tgcatttgta acgaattttt aaattcactt ttgtttatcc   660
gtcagattgt aagtactttc tctaatcact ttttttcaa ggcaatcagg gtatattata   720
ttgtacttca gcacagtttt agagaacaat tgttataatt aaatgataag gtagaatatt   780
tctgcatata aattctggct ggcgtggaaa tattcttatt ggtagaaaca actacatcct   840
ggtcatcatc ctgcctttct ctttatggtt acaatgatat acaccgtttg agatgaggat   900
aaaatactct gagtccaaac cgggcccctc tgctaaccat gttcatgcct tcttcttttt   960
cctacagctc ctgggcaacg tgctggttat tgtgccgcct catcattttg gcaaagaatt  1020
gtaatacgac tcactatagg gcgaattcag gttctgtgga caatcacaat gggaatccaa  1080
```

-continued

```
ggagggtctg tcctgttcgg gctgctgctc gtcctggctg tcttctgcca ttcaggtcat   1140
agcctgcaga gctacaaccc tccgcgtacg gactacaagg acgatgatga caaacagatc   1200
agcggtggag gctcagaagt ggagaagaca gcctgtcctt caggcaagaa ggcccgcgag   1260
atagacgaga gcctcatctt ctacaagaag tgggagctgg aagcctgcgt ggatgcggcc   1320
ctgctggcca cccagatgga ccgcgtgaac gccatcccct tcacctacga gcagctggac   1380
gtcctaaagc ataaactgga tgagctcggt ggaggctcag gtacgccacc tatgattttg   1440
agaacctctg aggaaaccat ttctacagtt caagaaaagc aacaaaatat ttctcccta    1500 gtgagagaaa gaggtcctca gagagtagca gctcacataa ctgggaccag aggaagaagc   1560
aacacattgc cttctccaaa ctccaagaat gaaaaggctc tgggccgcaa aataaactcc   1620
tgggaatcat caaggagtgg gcattcattc ctgagcaact tgcacttgag gaatggtgaa   1680
ctggtcatcc atgaaaaagg gttttactac atctattccc aaacatactt tcgatttcag   1740
gaggaaataa aagaaaacac aaagaacgac aaacaaatgg tccaatatat ttacaaatac   1800
acaagttatc ctgaccctat attgttgatg aaaagtgcta gaaatagttg ttggtctaaa   1860
gatgcagaat atggactcta ttccatctat caaggggaa tatttgagct taaggaaaat    1920
gacagaattc ttgtttctgt aacaaatgag cacttgatag acatggacca tgaagccagt   1980
tttttcgggg cctttttagt tggcagatcc caaaatattt ctcccctagt gagagaaaga   2040
ggtcctcaga gagtagcagc tcacataact gggaccagag gaagaagcaa cacattgtct   2100
tctccaaact ccaagaatga aaaggctctg gccgcaaaa taaactcctg gaatcatca    2160 aggagtgggc attcattcct gagcaacttg cacttgagga atggtgaact ggtcatccat   2220
gaaaaagggt tttactacat ctattcccaa acatactttc gatttcagga ggaaataaaa   2280
gaaaacacaa gaacgacaa acaaatggtc caatacactc acaaatacac aagtcatcct    2340
gaccctatat tgttgatgaa aagtgctaga aatagttgtt ggtctaaaga tgcagaatat   2400
ggactctatt ccatctatca agggggaata tttgagctta aggaaaatga cagaattttt   2460
gcttccgtaa caaatgagca cttgatagac atggaccatg aagccagttt tttcggggcc   2520
tttttagttg gcagatccca ccaccaccac caccaccaaa atatttctcc cctagtgaga   2580
gaaagaggtc ctcagagagt agcagctcac ataactggga ccagaggaag aagcaacaca   2640
ttgtcctctc caaactccaa gaatgaaaag gctctgggcc gcaaaataaa ctcctgggaa   2700
tcatcaagga gtgggcattc attcctgagc aacttgcact tgaggaacgg tgaactggtc   2760
atccatgaaa aagggtttta ctacatctat tcccaaacat actttcgatt tcaggaggaa   2820
ataaaagaaa acacaaagaa cgacaaacaa atggtccaat atatctacaa atacacaagt   2880
tatcctgacc ctatattgtt gatgaaaagt gctagaaata gttgttggtc taaagatgca   2940
gaatatggac tctattccat ctatcaaggg ggaatatttg agcttaagga aaatgacaga   3000
atttttgttc ctgtaacaaa tgagcacttg atagacatgg accacgaagc cagtttttc    3060 ggggcctttt tagttggcag atcttaatct aggatcttat caaagcagaa cttgtttact   3120
gcagcttata atggttacaa ataaagcaat agcatcacaa atttcacaaa taagcatttt   3180
ttttcactgc attctagttg tggtttgtcc aaactcatca atgtatctta tcatgtctgg   3240
tcgaccctag actcttccgc ttcctcgctc actgactcgc tgcgctcggt cgttcggctg   3300
cggcgagcgg tatcagctca ctcaaaggcg gtaatacggc catccacaga atcagggat    3360 aacgcaggaa agaacatgtg agcaaaaggc cagcaaaagg ccaggaaccg taaaaaggcc   3420
gcgttgctgc cgttttccca taggctccgc cccctgacg agcatcacaa aatcgacgc     3480 tcaagtcaga ggtggcgaaa cccgacagga ccataaagat accaggcgtt ccccctgga    3540
```

-continued

```
agctccctcg tgcgctctcc tgttccgacc ctgccgctta ccggatacct gtccgccttt   3600 ctccctcgg gaagcgtggc gctttctcaa tgctcacgct gtaggtatct cagttcggcg    3660
taggtcgttc gctccaagct gggctgtgtg cacgaacccc ccgttcagcc cgaccgctgc   3720
gccttatccg gtaactatcg tcttgagtcc aacccggtaa gacacgactt atcgccactg   3780
gcagcagcca ctggtaacag gattagcaga gcgaggtatg caggcggtgc tacagagtcc   3840
ttgaagtggt ggcctaacta cggctacact agaaggacag tatttggtat ctgcgctctg   3900
ctgaagccag ttaccttcgg aaaaagagtt ggtagctctt gatccggcaa acaaaccacc   3960
gctggtagcg gtggtttttt tgtttgcaag cagcagatta cgcgcagaaa aaaggatct   4020 caagaagatc ctctgatctt ttctacgggg tctgacgctc agtggaacga aaactcacgt   4080
taagggattt tggtcatgag attatcaaaa aggatcttca cctagatcct tttaaattaa   4140
aaatgaagtt ttaaatcaat ctaaagtata tatgagtaaa cttggtctga cagttaccaa   4200
tgcttaatca gtgaggcacc tatctcagcg atctgtctat ttcgttcatc catagttgcc   4260
tgactccccg tcgtgtagat aactacgata cgggagggct caccatctgg ccccagtgct   4320
gcaatgatac cgcgagaccc acgctcaccg gctccagatt tatcagcaat aaaccagcca   4380 gccgaaggg ccgagcgcag aagtggtcct gcaacctcat ccgcctccat ccagtctatt    4440
aattgccgcc gggaagctag agtaagtagt tcgccagtta atagtttgcg caacgttgtt   4500
gccattgcta caggcatcgt ggtgtcacgc tcgtcgtttg gtatggcttc attcagctcc   4560
ggttcccaac gatcaaggcg agttacatga tcccccatgt tgtgcaaaaa agcggttagc   4620
tccttcggtc ctccgatcgt tgtcagaagt aagttggccg cagtgttatc actcatggtt   4680
atggcagcac tgcataattc tcttactgtc atgccatccg taagatgctt ttctgtgact   4740
ggtgagtact caaccaagtc attctgagaa tagtgtatgc ggcgaccgag ttgctcttgc   4800
ccggcgtcaa tacgggataa taccgcgcca catagcagaa cttttaaagt gctcatcatt   4860
ggaaaacgtc cttcggggcg aaaactctca aggatcttac cgctgttgag atccagttcg   4920
atgtaaccca ctcgtgcacc caactgatct tcagcatctt ttactttcac cagcgtttct   4980
gggtgagcaa aaacaggaag gcaaaatgcc gcaaaaaagg gaataagggc gacacggaaa   5040
tgttgaatac tcatactctt cttttttcaa tattattgaa gcatttatca gggttattgt   5100
ctcatgagcg gatacatatt tgaatgtatt tagaaaaata acaaataggg gttccgcgc    5160 acatttcccc gaaaagtgcc acctgacgtc taagaaacca ttattatcat gacattaacc   5220
tataaaaata ggcgtatcac gaggccccttt tcgtctcgcg cgtttcggtg atgacggtga   5280
aaacctctga cacatgcagc tcccggagac ggtcacagct tgtctgtaag cggatgccgg   5340
gagcagacaa gcccgtcagg gcgcgtcagc gggtgttggc gggtgtcggg gctggcttaa   5400
ctatgcggca tcagagcaga ttgtactgag agtgcaccat atgcggtgtg aaataccgca   5460
cagatgcgta aggagaaaat accgcatcag gaaattgtaa acgttaatat tttgttaaaa   5520
ttcgcgttaa atttttgtta aatcagctca tttttaacc aataggccga aatcggcaaa    5580
atcccttata atcaaaaga atagaccgag atagggttga gtgttgttcc agtttggaac    5640
aagagtccac tattaaagaa cgtggactcc aacgtcaaag ggcgaaaaac cgtctatcag   5700
ggcgatggcc cactacgtga accatcaccc taatcaagtt ttttggggtc gaggcgccgt   5760
aaagcactaa atcggaaccc taagggagc ccccgattta gagcttgacg gggaaagccg    5820
gcgaacgtgg cgagaaagga agggaagaaa gcgaaaggag cgggcgctag ggcgctggca   5880
agtgtagcgc tcacgctgcg cgtaaccacc acacccgccg cgcttaatgc gccgctacag   5940
ggcgcgtcgc gccattcgcc attcaggcta cgcaactgtt gggaagggcg atcggtgcgg   6000
```

-continued

Figure 11:
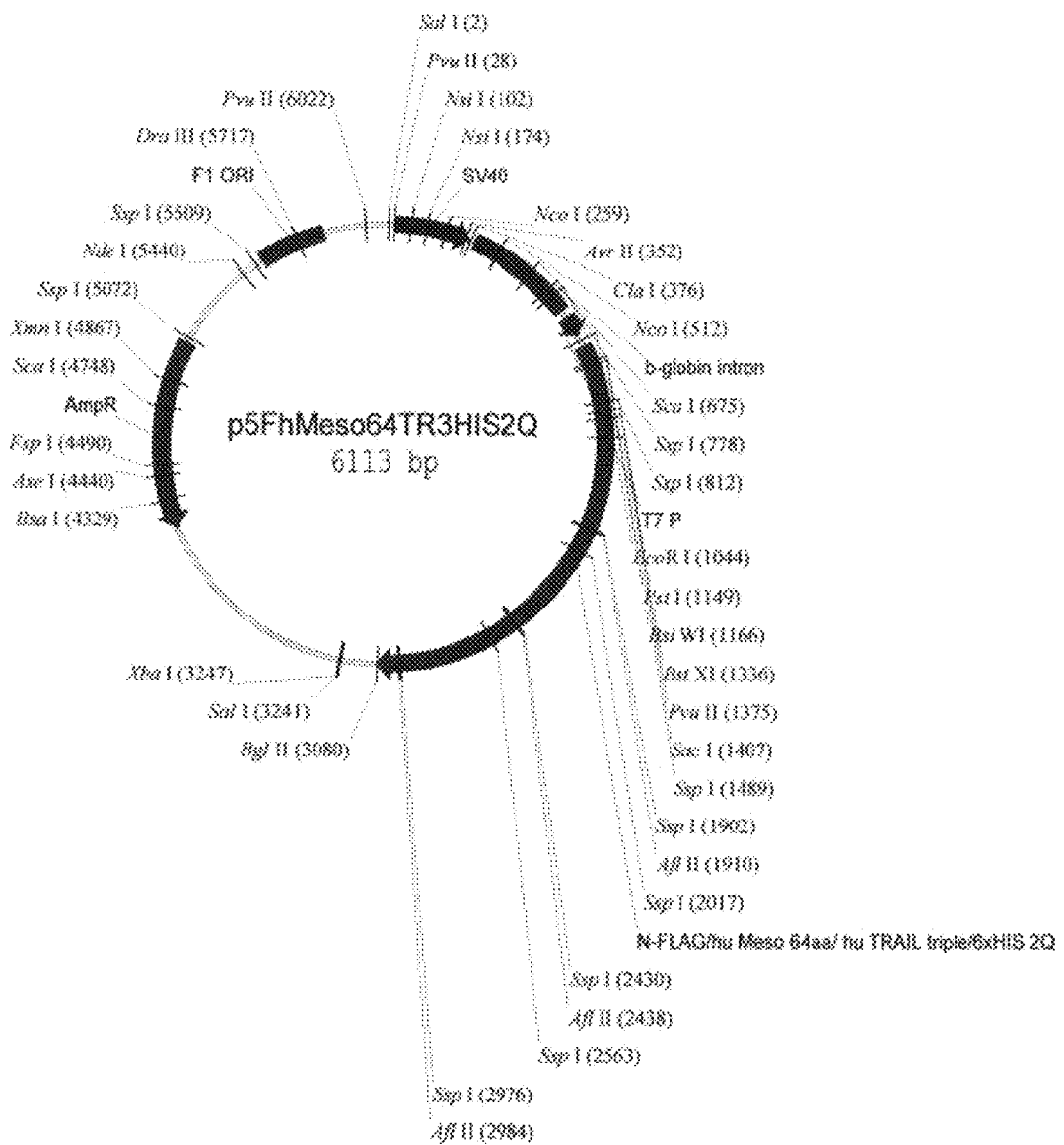
FIG. 11 illustrates a restriction map of plasmid p5FhMeso1TR3HIS2Q.
Figure 12A:
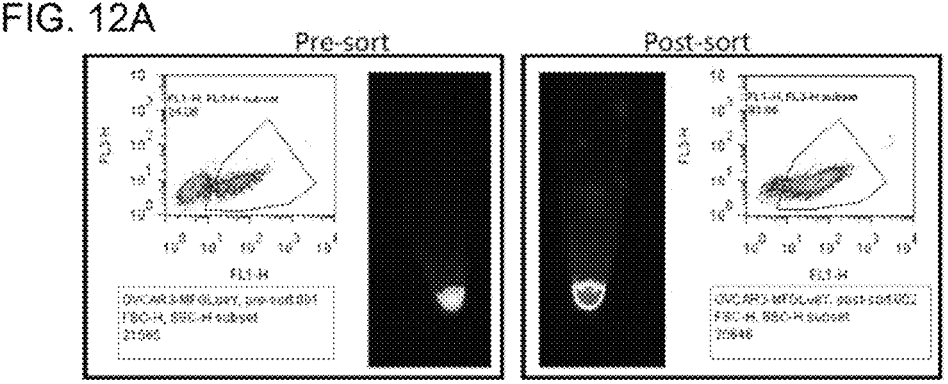
FIG. 12A-D illustrate reduction of tumor burden by Meso-TR3 in an in vivo model of ovarian cancer.
Figure 12B:
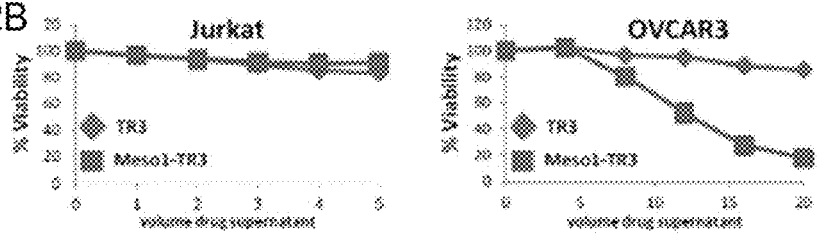
Figure 12C:
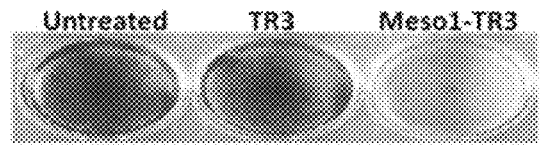
Figure 12D:
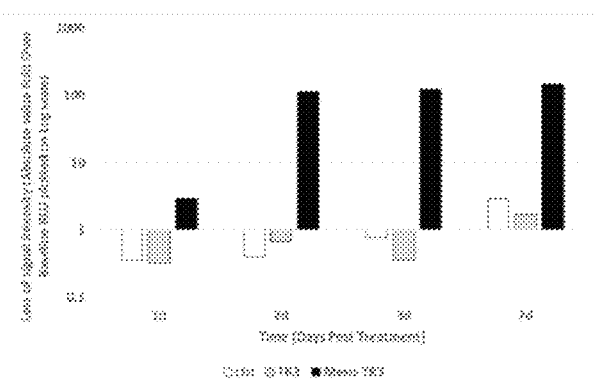

```
gcctcttcgc tattacgcca gctggcgaag gggggatgtg ctgcaaggcg attaagttgg   6060
gtaacgccag ggttttccca gtcacgacgt tgtaaaacga cggccagtga att          6113
``` p5FhMeso1TR3HIS2Q (6767 BP) (FIG.11):

(SEQ ID NO: 3)

```
gtcgacttct gaggcggaaa gaaccagctg tggaatgtgt gtcagttagg gtgtggaaag     60
tccccaggct ccccagcagg cagaagtatg caaagcatgc atctcaatta gtcagcaacc    120
aggtgtggaa agtccccagg ctccccagca ggcagaagta tgcaaagcat gcatctcaat    180
tagtcagcaa ccatagtccc gcccctaact ccgcccatcc cgcccctaac tccgcccagt    240
tccgcccatt ctccgcccca tggctgacta atttttttta tttatgcaga ggccgaggcc    300
gcctcggccc ctgagctatt ccagaagtag tgaggaggct ttttggagg cctaggcttt     360 tgcaaaaagc tggatcgatc ctgagaactt cagggtgagt ctggggaccc ttgattgtcc    420 tttcttttc gctattgtaa aattcatgtt atatggaggg gcaaagtttt caggggtgtt     480
gtttagaatg ggaagatgtc ccttgtatca ccatggaccc tcatgataat tttgtttctt    540
tcactctcta ctctgttgac aaccattgtc tcctcttatt ctcttttcat tttctgtaac    600
tttttcgtta aactttagct tgcatttgta acgaattttt aaattcactt ttgtttatcc    660
gtcagattgt aagtactttc tctaatcact ttttttcaa ggcaatcagg gtatattata     720
ttgtacttca gcacagtttt agagaacaat tgttataatt aaatgataag gtagaatatt    780
tctgcatata aattctggct ggcgtggaaa tattcttatt ggtagaaaca actacatcct    840
ggtcatcatc ctgcctttct ctttatggtt acaatgatat acaccgtttg agatgaggat    900
aaaatactct gagtccaaac cgggcccctc tgctaaccat gttcatgcct cttctttt     960 cctacagctc ctgggcaacg tgctggttat tgtgccgcct catcattttg gcaaagaatt   1020
gtaatacgac tcactatagg gcgaattcag gttctgtgga caatcacaat gggaatccaa   1080
ggagggtctg tcctgttcgg gctgctgctc gtcctggctg tcttctgcca ttcaggtcat   1140
agcctgcaga gctacaaccc tccgcgtacg gactacaagg acgatgatga caaacagatc   1200
agcggtggag gctcagaagt ggagaagaca gcctgtcctt caggcaagaa ggcccgcgag   1260
atagacgaga gcctcatctt ctacaagaag tgggagctgg aagcctgcgt ggatgcggcc   1320
ctgctggcca cccagatgga ccgcgtgaac gccatcccct tcacctacga gcagctggac   1380
gtcctaaagc ataaactgga tgagctcggt ggaggctcag gtacgccacc tatgattttg   1440
cacctgggct acctcttcct caagatgagc cctgaggaca ttcgcaagtg gaatgtgacg   1500
tccctggaga ccctgaaggc tttgcttgaa gtcaacaaag ggcacgaaat gagtcctcag   1560
aacacattgc cttctccaaa ctccaagaat gaaaaggctc cgggccgcaa aataaactcc   1620
tgggaatcat caaggagtgg gcattcattc ctgagcaact gcacttgag gaatggtgaa    1680 ctggtcatcc atgaaaaagg gttttactac atctattccc aaacatactt tcgatttcag   1740
gaggaaataa agaaaacac aaagaacgac aaacaaatgg tccaatatat ttacaaatac    1800
acaagttatc ctgaccctat attgttgatg aaaagtgcta gaaatagttg ttggtctaaa   1860
gatgcagaat atggactcta ttccatctat caaggggaa tatttgagct taaggaaaat    1920
gacagaattt ttgtttctgt aacaaatgag cacttgatag acatggacca tgaagccagt   1980
tttttcgggg cctttttagt tggcagatcc caaaatattt ctcccctagt gagagaaaga   2040
ggtcctcaga gagtagcagc tcacataact ggaccagaga agaagcaa cacattgtct     2100 tctccaaact ccaagaatga aaaggctctg gccgcaaaa taaactcctg ggaatcatca    2160
aggagtgggc attcattcct gagcaacttg cacttgagga atggtgaact ggtcatccat   2220
gaaaaagggt ttactacat ctattcccaa acatactttc gatttcagga ggaaataaaa    2280
```

-continued

```
gaaaacacaa agaacgacaa acaaatggtc caatacactc acaaatacac aagtcatcct   2340
gaccctatat tgttgatgaa aagtgctaga aatagttgtt ggtctaaaga tgcagaatat   2400
ggactctatt ccatctatca aggggaata  tttgagctta aggaaaatga cagaattttt   2460
gcttccgtaa caaatgagca cttgatagac atggaccatg aagccagttt tttcggggcc   2520
tttttagttg gcagatccca ccaccaccac caccaccaaa atatttctcc cctagtgaga   2580
gaaagaggtc ctcagagagt agcagctcac ataactggga ccagaggaag aagcaacaca   2640
ttgtcctctc caaactccaa gaatgaaaag gctctgggcc gcaaaataaa ctcctgggaa   2700
tcatcaagga gtgggcattc attcctgagc aacttgcact cgaggaacgg tgaactggtc   2760
atccatgaaa aagggtttta ctacatctat tcccaaacat actttcgatt tcaggaggaa   2820
ataaaagaaa acacaaagaa cgacaaacaa atggtccaat atatctacaa atacacaagt   2880
tatcctgacc ctatattgtt gatgaaaagt gctagaaata gttgttggtc taaagatgca   2940
gaatatggac tctattccat ctatcaaggg ggaatatttg agcttaagga aaatgacaga   3000 attttgttc  ctgtaacaaa tgagcacttg atagacatgg accacgaagc cagttttttc   3060
ggggcctttt tagttggcag atcttaatct aggatcttat caaagcagaa cttgtttact   3120
gcagcttata atggttacaa ataaagcaat agcatcacaa atttcacaaa taaagcattt   3180
ttttcactgc attctagttg tggtttgtcc aaactcatca atgtatctta tcatgtctgg   3240
tcgaccctag actcttccgc ttcctcgctc actgactcgc tgcgctcggt cgttcggctg   3300
cggcgagcgg tatcagctca ctcaaaggcg gtaatacggc catccacaga atcaggggat   3360
aacgcaggaa agaacatgtg agcaaaaggc cagcaaaagg ccaggaaccg taaaaaggcc   3420
gcgttgctgg cgttttttcca taggctccgc ccccctgacg agcatcacaa aaatcgacgc   3480
tcaagccaga ggtggcgaaa cccgacagga ccataaagat accaggcgtt ccccctgga   3540 agctccctcg tgcgctctcc tgttccgacc ctgccgctta ccggatacct gtccgccttt   3600
ctcccctcgg gaagcgtggc gctttctcaa tgctcacgct gtaggtatct cagttcggcg   3660
taggtcgttc gctccaagct gggctgtgtg cacgaacccc ccgttcagcc cgaccgctgc   3720
gccttatccg gtaactatcg tcttgagtcc aacccggtaa gacacgactt atcgccactg   3780
gcagcagcca ctggtaacag gattagcaga gcgaggtatg caggcggtgc tacagagtcc   3840
ttgaagtggt ggcctaacta cggctacact agaaggacag tatttggtat ctgcgctctg   3900
ctgaagccag ttaccttcgg aaaaagagtt ggtagctctt gatccggcaa acaaaccacc   3960
gctggtagcg gtggtttttt tgtttgcaag cagcagatta cgcgcagaaa aaaggatctc   4020
caagaagatc ctctgatctt ttctacgggg tctgacgctc agtggaacga aaactcacgt   4080
taagggattt tggtcatgag attatcaaaa aggatcttca cctagatcct tttaaattaa   4140
aaatgaagtt ttaaatcaat ctaaagtata tatgagtaaa cttggtctga cagttaccaa   4200
tgcttaatca gtgaggcacc tatctcagcg atctgtctat ttcgttcatc catagttgcc   4260
tgactccccg tcgtgtagat aactacgata cgggagggct caccatctgg ccccagtgct   4320
gcaatgatac cgcgagaccc acgctcaccg gctccagatt tatcagcaat aaaccagcca   4380
gccggaaggg ccgagcgcag aagtggtcct gcaacctcat ccgcctccat ccagtctatt   4440
aattgctgcc gggaagctag agtaagtagt tcgccagtta atagtttgcg caacgttgtt   4500
gccattgcta caggcatcgt ggtgtcacgc tcgtcgtttg gtatggcttc attcagctcc   4560
ggttcccaac gatcaaggcg agttacatga tcccccatgt tgtgcaaaaa agcggttagc   4620
tccttcggtc ctccgatcgt tgtcagaagt aagttggccg cagtgttatc actcatggtt   4680
atggcagcac tgcataattc tcttactgtc atgccatccg taagatgctt ttctgtgact   4740
```

-continued

```
ggtgagtact caaccaagtc attctgagaa tagtgtatgc ggcgaccgag ttgctcttgc    4800
ccggcgtcaa tacgggataa taccgcgcca catagcagaa ctttaaaagt gctcatcatt    4860
ggaaaacgtc cttcggggcg aaaactctca aggatcttac cgctgttgag atccagttcg    4920
atgtaaccca ctcgtgcacc caactgatct tcagcatctt ttactttcac cagcgtttct    4980
gggtgagcaa aaacaggaag gcaaaatgcc gcaaaaaagg gaataagggc gacacggaaa    5040
tgttgaatac tcatactctt ctttttcaa tattattgaa gcatttatca gggttattgt       5100
ctcatgagcg gatacatatt tgaatgtatt tagaaaaata acaaataggg gttccgcgc       5160 acatttcccc gaaaagtgcc acctgacgtc taagaaacca ttattatcat gacattaacc    5220
tataaaaata ggcgtatcac gaggcccctt tcgtctcgcg cgtttcggtg atgacggtga    5280
aaacctctga cacatgcagc tcccggagac ggtcacagct tgtctgtaag cggatgccgg    5340
gagcagacaa gcccgtcagg gcgcgtcagc gggtgttggc gggtgtcggg gctggcttaa    5400
ctatgcggca tcagagcaga ttgtactgag agtgcaccat atgcggtgtg aaataccgca    5460
cagatgcgta aggagaaaat accgcatcag gaaattgtaa acgttaatat tttgttaaaa    5520
ttcgcgttaa attttgtta aatcagctca ttttttaacc aataggccga atcggcaaa       5580 atcccttata aatcaaaaga atagaccgag atagggttga gtgttgttcc agtttggaac    5640
aagagtccac tattaaagaa cgtggactcc aacgtcaaag ggcgaaaaac cgtctatcag    5700
ggcgatggcc cactacgtga accatcaccc taatcaagtt ttttggggtc gaggcgccgt    5760
aaagcactaa atcggaaccc taaagggagc cccgatttta gagcttgacg gggaaagccg    5820
gcgaacgtgg cgagaaagga agggaagaaa gcgaaaggag cgggcgctag gcgctggca    5880 agtgtagcgg tcacgctgcg cgtaaccacc acccgccg cgcttaatgc gccgctacag       5940
ggcgcgtcgc gccattcgcc attcaggcta cgcaactgtt gggaagggcg atcggtgcgg    6000
gcctcttcgc tattacgcca gctggcgaag gggatgtg ctgcaaggcg attaagttgg       6060
ggcatcagag cagattgtac tgagagtgca ccatatgcgg tgtgaaatac cgcacagatg    6120
cgtaaggaga aataccgca tcaggaaatt gtaaacgtta atattttgtt aaaattcgcg    6180
ttaaattttt gttaaatcag ctcattttttt aaccaatagg ccgaaatcgg caaaatccct    6240
tataaatcaa agaatagac cgagataggg ttgagtgttg ttccagtttg gaacaagagt    6300
ccactattaa agaacgtgga ctccaacgtc aaagggcgaa aaaccgtcta tcagggcgat    6360
ggcccactac gtgaaccatc accctaatca agttttttgg ggtcgaggtg ccgtaaagca    6420
ctaaatcgga accctaaagg agccccccga tttagagctt gacggggaaa gccggcgaac    6480
gtggcgagaa aggaagggaa gaaagcgaaa ggagcgggcg ctagggcgct ggcaagtgta    6540
gcggtcacgc tgcgcgtaac caccacaccc gccgcgctta atgcgccgct acagggcgcg    6600
tcgcgccatt cgccattcag gctacgcaac tgttgggaag ggcgatcggt gcgggcctct    6660
tcgctattac gccagctggc gaaggggga tgtgctgcaa ggcgattaag ttgggtaacg      6720
ccagggtttt cccagtcacg acgttgtaaa acgacggcca gtgaatt                   6767
``` p5TR3HIS2Q (5858 BP):
(SEQ ID NO: 4)

```
gtcgacttct gaggcggaaa gaaccagctg tggaatgtgt gtcagttagg gtgtggaaag      60
tccccaggct ccccagcagg cagaagtatg caaagcatgc atctcaatta gtcagcaacc     120
aggtgtggaa agtccccagg ctccccagca ggcagaagta tgcaaagcat gcatctcaat     180
tagtcagcaa ccatagtccc gcccctaact ccgcccatcc cgcccctaac tccgcccagt     240
tccgcccatt ctccgcccca tggctgacta attttttta tttatgcaga ggccgaggcc     300
gcctcggcct ctgagctatt ccagaagtag tgaggaggct ttttttggagg cctaggcttt    360
```

-continued

```
tgcaaaaagc tggatcgatc ctgagaactt cagggtgagt ttggggaccc ttgattgttc    420 tttcttttttc gctattgtaa aattcatgtt atatggaggg ggcaaagttt tcagggtgtt    480
gtttagaatg ggaagatgtc ccttgtatca ccatggaccc tcatgataat tttgtttctt    540
ccactttcta ctctgttgac aaccattgtc tcctcttatt ttcttttcat tttctgtaac    600
ctctccgtta aactttagct tgcatttgta acgaattctc aaatccaccc ttgtttattt    660
gtcagattgt aagtactttc tctaatcact ttttttttcaa ggcaatcagg gtatattata    720
ttgtacttca gcacagtttt agagaacaat tgttataatt aaatgataag gtagaatatt    780
tctgcacata aattctggct ggcgtggaaa tattcttatt ggtagaaaca actacatcct    840
ggtcatcatc ctgcctttct ctttatggtt acaatgatat acactgtttg agatgaggat    900
aaaatactct gagtccaaac cgggcccctc tgctaaccat gttcatgcct tcttcttttt    960
cctacagctc ctgggcaacg tgctggttat tgtgctgtct catcattttg gcaaagaatt   1020
gtaatacgac tcactatagg gcgaattcag gttctgtgga caatcacaat gggaatccaa   1080
ggagggtctg tcctgttcgg gctgctgctc gtcctggctg tcttctgcca ttcaggtcat   1140
agcctgcaga gctacaaccc tccgcgtacg gactacaagg acgatgatga caaacagatc   1200
agcggtggag gctcagaagt ggagaagaca gcctgtcctt caggcaagaa ggcccgcgag   1260
atagacgaga gcctcatctt ctacaagaag tgggagctgg aagcctgcgt ggatgcggcc   1320
ctgctggcca cccagatgga ccgcgtgaac gccatcccct tcacctacga gcagctggac   1380
gtcctaaagc ataaactgga tgagctctac ccacaaggtt accccgagtc tgtgatccag   1440
cacctgggct acctcttcct caagatgagc cctgaggaca ttcgcaagtg aatgtgacgc   1500
tccctggaga ccctgaaggc tttgcttgaa gtcaacaaag ggcacgaaac gagtcctcag   1560
gtggccaccc tgatcgaccg cttttgtgaag ggaaggggcc agctagacaa agacacccta   1620
gacaccctga ccgccttcta ccctgggtac ctgtgctccc tcagcccgga ggagctgagc   1680
tccgtgcccc ccagcagcat ctgggcggtc aggcccagg acctggacac gtgtgaccca   1740
aggcagctgg acgtcctcta tcccaaggcc cgccttgctt tccagaacat gaacgggtcc   1800
gaatacttcg tgaagatcca gtccttcctg ggtggggccc ccacggagga tttgaaggcg   1860
ctcagtcagc agaatgtgag catggacttg gccacgttca tgaagctgcg gacggatgcg   1920
gtgctgccgt tgactgtggc tgaggtgcag aaacttctgg accccacgt ggagggcctg   1980 aaggcggagg agcggcaccg cccggtgcgg gactggatcc tacggcagcg gcaggacgac   2040
ctggacacgc tgggctggg gctacagggc ctgcgtacgc cacctatgat tttgagaacc   2100
tctgaggaaa ccatttctac agttcaagaa aagcaacaaa atatttctcc cctagtgaga   2160
gaaagaggtc ctcagagagt agcagctcac ataactggga ccagaggaag aagcaacaca   2220
ttgtcttctc caaactccaa gaatgaaaag gctctgggcc gcaaaataaa ctcccgggaa   2280
tcatcaagga gtgggcattc attcctgagc aacttgcact tgaggaatgg tgaactggtc   2340
atccatgaaa aagggtttta ctacatctat tcccaaacat actttcgatt tcaggaggaa   2400 ataaagaaa acacaaagaa cgacaaacaa atggtccaat atatttacaa atacacaagt   2460
tatcctgacc ctatattgtt gatgaaaagt gctagaaata gttgttggtc taaagatgca   2520
gaatatggac tctattccat ctatcaaggg ggaatatttg agcttaagga aaatgacaga   2580 attttttgttt ctgtaacaaa tgagcacttg atagacatgg accatgaagc cagttttttc   2640 ggggccttt tagttggcag atcccaaaat atttctcccc tagtgagaga aagaggtcct   2700
cagagagtag cagctcacat aaccgggacc agaggaagaa gcaacacatt gtctcctcca   2760
aactccaaga atgaaaaggc tctgggccgc aaaataaact cctgggaatc atcaaggagt   2820
```

-continued

```
gggcattcat tcctgagcaa cttgcacttg aggaatggtg aactggtcat ccatgaaaaa   2880
gggttctacc acatctattc ccaaacatac tttcgatttc aggaggaaat aaaagaaaac   2940
acaaagaacg acaaacaaat ggtccaatat atttacaaat acacaagtta tcctgaccct   3000
atattgttga tgaaaagtgc tagaaatagt tgttggtcta agatgcaga atatggactc    3060 cattccatct atcaagggggg aatatttgag cttaaggaaa atgacagaat ttttgtttct  3120
gtaacaaatg agcacttgat agacatggac catgaagcca gttttttcgg ggccttttta   3180
gttggcagat cccaccacca ccaccaccac caaaatattt ctcccctagt gagagaaaga   3240
ggtcctcaga gagtagcagc tcacataact gggaccagag gaagaagcaa cacattgcct   3300
tctccaaact ccaagaatga aaaggctctg gccgcaaaa taaactcctg ggaatcatca    3360
aggagtgggc attcattcct gagcaacttg cacttgagga atggtgaact ggtcatccat   3420
gaaaaagggt tttactacat ctactcccaa acatactttc gattccagga ggaaataaaa   3480
gaaaacacaa agaacgacaa acaaatggtc caatatattt acaaatacac aagttatcct   3540
gaccctatat tgttgatgaa aagtgctaga atagttgtt ggtctaaaga tgcagaatat    3600
ggactctatt ccatctatca aggggggaata tttgagctta aggaaaatga cagaattttt  3660
gtttccgtaa caaatgagca cttgatagac atggaccatg aagccagttt ttcgggggcc   3720
tttttagttg gcagatctta atctaggatc ttattaaagc agaacttgtt cattgcagct   3780
tataatggtt acaaataaag caatagcatc acaaatttca caaataaagc attttttttca  3840 ctgcattcta gttgtggttt gtccaaactc atcaatgtat cttatcatgc ctggtcgact   3900
ctagactctt ccgcttcctc gctcactgac tcgctgcgct cggtcgttcg gctgcggcga   3960
gcggtatcag ctcactcaaa ggcggtaata cggttatcca cagaatcagg ggataacgca   4020
ggaaagaaca tgtgagcaaa aggccagcaa aaggccagga accgtaaaaa ggccgcgtcg   4080
ctggcgtttt tccataggct ccgcccccct gacgagcatc acaaaaatcg acgctcaagt   4140
cagaggtggc gaaacccgac aggactataa agataccagg cgttccccccc tggaagctcc   4200 ctcgtgcgct ctcctgttcc gaccctgccg cttaccggat acctgtccgc ctttctccct   4260
tcgggaagcg tggcgctttc tcaatgctca cgctgtaggt atctcagttc ggtgtaggtc   4320
gttcgctcca agctgggctg tgtgcacgaa ccccccgttc agcccgaccg ctgcgcctta   4380
tccggtaact atcgtcttga gtccaacccg gtaagacacg acttatcgcc actggcagca   4440
gccactggta acaggattag cagagcgagg tatgtaggcg gtgctacaga gttcttgaag   4500
tggtggccta actacggcta cactagaagg acagtatttg gtatctgcgc tctgctgaag   4560
ccagtcacct tcggaaaaag agttggtagc tcttgatccg gcaaacaaac caccgctggt   4620
agcggtggtt ttttttgtttg caagcagcag attacgcgca gaaaaaaagg atctcaagaa   4680
gatcctttga tcttttctac ggggtctgac gctcagtgga acgaaaactc acgttaaggg   4740
attttggtca tgagattatc aaaaaggatc ttcacctaga tccttttaaa ttaaaaatga   4800
agttttaaat caatctaaag tatatatgag taaacctggt ctgacagtta ccaatgctta   4860
atcagcgagg cacctatctc agcgatctgt ctatttcgtt catccatagt tgcctgaccc   4920
cccgtcgtgt agataactac gatacgggag ggcttaccat ctggccccag tgctgcaacg   4980
ataccgcgag acccacgctc accggctcca gatttatcag caataaacca gccagccgga   5040
agggccgagc gcagaagtgg tcctgcaact ttatccgcct ccatccagtc tattaattgt   5100
tgccgggaag ctagagtaag tagttcgcca gttaatagtt tgcgcaacgt tgttgccatt   5160
gctacaggca tcgtggtgtc acgctcgtcg tttggtatgg cttcattcag ctccggttcc   5220
caacgatcaa ggcgagttac atgatccccc atgttgtgca aaaaagcggt tagctccttc   5280
```

```
ggtcctccga tcgttgtcag aagtaagttg gccgcagtgt tatcactcat ggttatggca    5340
gcactgcata attctcttac tgtcatgcca tccgtaagat gcttttctgt gactggtgag    5400
tactcaacca agtcattctg agaatagtgt atgcggcgac cgagttgctc ttgcccggcg    5460
tcaatacggg ataataccgc gccacatagc agaactttaa aagtgctcat cattggaaaa    5520
cgttcttcgg ggcgaaaact ctcaaggatc ttaccgctgt tgagatccag ttcgatgtaa    5580
cccactcgtg cacccaactg atcttcagca tcttttactt tcaccagcgt ttctgggtga    5640
gcaaaaacag gaaggcaaaa tgccgcaaaa aagggaataa gggcgacacg gaaatgttga    5700
atactcatac tcttcttttt tcaatattat tgaagcactt atcagggtta ttgtctcatg    5760
cgccagctgg cgaaggggggg atgtgctgca aggcgattaa gttgggtaac gccagggttt    5820
tcccagtcac gacgttgtaa aacgacggcc agtgaatt                            5858
```

Polypeptides with anti-tumor activity of the present teachings include, without limitation, polypeptides of the following sequences. His tags, when present, are indicated with bold typeface.

TR3
(SEQ ID NO: 5)
MGIQGGSVLFGLLLVLAVFCHSGHSLQSYNPPRTPPMILRTSEETISTVQEKQQNISPLVR

ERGPQRVAAHITGTRGRSKTLSSPNSKNEKALGRKINSWESSRSGHSFLSNLHLRNGELV

IHEKGFYYIYSQTYFRFQEEIKENTKNDKQMVQYIYKYTSYPDPILLMKSARNSCWSKD

AEYGLYSIYQGGIFELKENDRIFVSVTNEHLIDMDHEASFFGAFLVGRSQNISPLVRERGP

QRVAAHITGTRGRSNTLSSPNSKNEKALGRKINSWESSRSGHSFLSNLHLRNGELVIHEK

GFYYIYSQTYFRFQEEIKENTKNDKQMVQYIYKYTSYPDPILLMKSARNSCWSKDAEYG

LYSIYQGGIFELKENDRIFVSVTNEHLIDMDHEASFFGAFLVGRSQNISPLVRERGPQRVA

AHITGTRGRSNTLSSPNSKNEKALGRKINSWESSRSGHSFLSNLHLRNGELVIHEKGFYYI

YSQTYFRFQEEIKENTKNDKQMVQYIYKYTSYPDPIIXMKSARNSCWSKDAEYGLYSIY

QGGIFELKENDRIFVSVTNEHLIDMDHEASFFGAFLVGRS

TR3-HIS
(SEQ ID NO: 6)
MGIQGGSVLFGLLLVLAVFCHSGHSLQSYNPPRTPPMILRTSEETISTVQEKQQNISPLVR

ERGPQRVAAHITGTRGRSNTLSSPNSKNEKALGRKFNSWESSRSGHSFLSNLHLRNGELV

IHEKGFYYIYSQTYFRFQEEIKENTKNDKQMVQYIYKYTSYPDP1LLMKSARNSCWSKD

AEYGLYSIYQGGIFELKENDRIFVSVTNEHLIDMDHEASFFGAFLVGRSQNISPLVRERGP

QRVAAHITGTRGRSNTLSSPNSKNEKALGRKINSWESSRSGHSFLSNLHLRNGELVIHEK

GFYYIYSQTYFRFQEEIKENTKNDKQMVQYIYKYTSYPDPILLMKSARNSCWSKDAEYG

LYSIYQGGIFELKENDRIFVSVTNEHLIDMDHEASFFGAFLVGRSQNISPLVRERGPQRVA

AHITGTRGRSNTLSSPNSKNEKALGRKINSWESSRSGMSFLSNLHLRNGELVIHEKGFYYI

YSQTYFRFQEEIKENTKNDKQMVQYIYKYTSYPDPILLMKSARNSCWSKDAEYGLYSTY

QGGIFELKENDRIFVSVTNEHLIDMDHEASFFGAFLVGGGGSHHHHHHRS

TR3-HIS2Q
(SEQ ID NO: 7)
MGIQGGSVLFGLLLVLAVFCHSGHSLQSYNPPRTPPMILRTSEETISTVQEKQQNISPLVR

ERGPQRVAAHITGTRGRSNTLSSPNSKNEKALGRKINSWESSRSGHSFLSNLHLRNGELV

IHEKGFYYIYSQTYFRFQEEIKENTKNDKQMVQYIYKYTSYPDPILLMKSARNSCWSKD

AEYGLYSIYQGGIFELKENDRIFVSVTNEHLIDMDHEASFFGAFLVGRSQNISPLVRERGP

-continued

QRVAAHITGTRGRSNTLSSPNSKNEKALGRKINSWESSRSGHSFLSNLHLRNGELV1HEK

GFYYIYSQTYFRFQEEIKENTKNDKQMVQYIYKYTSYPDPILLMKSARNSCWSKDAEYG

LYSIYQGGIFELKENDRIFVSVTNEHLIDMDHEASFFGAFLVGRSHHHHHHQNISPLVRE

RGPQRVAAHITGTRGRSNTLSSPNSKNEICALGRKINSWESSRSGHSFLSNLHLRNGELVI

HEKGFYYIYSQTYFRFQEEIKENTKNDKQMVQYIYKYTSYPDPILLMKSARNSCWSKDA

EYGLYSIYQGGIFELKENDRIFVSVTNEHLIDMDHEASFFGAFLVGRS

TR3-HIS2V
(SEQ ID NO: 8)
MGIQGGSVLFGLLLVLAVFCHSGHSLQSYNPPRTPPMILRTSEETISTVQEKQQNISPLVR

ERGPQRVAAHiTGTRGRSNTLSSPNSKNEKALGRKINSWESSRSGHSFLSNLHLRNGELV

IHEKGFYYIYSQTYFRFQEEIKENTKNDKQMVQYIYKYTSYPDPILLMKSARNSCWSKD

AEYGLYSIYQGGIFELKENDRIFVSVTNEMLIDMDHEASFFGAFLVGRSQNISPLVRERGP

QRVAAHITGTRGRSNTLSSPNSKNEKALGRKJNSWESSRSGHSFLSNLHLRNGELVIHEK

GFYY1YSQTYFRFQEEIKENTKNDKQMVQYIYKYTSYPDPILLMKSARNSCWSKDAEYG

LYSIYQGGIFELKENDRIFVSVTNEHLIDMDHEASFFGAFLVGRSHHHHHHVRERGPQK

VAAHITGTRGRSNTLSSPNSKNEKALGRKINSWESSRSGHSFLSNLHLRNGELVIHEKGF

YYIYSQTYFRFQEEIKENTKNDKQMVQYIYKYTSYPDPILLMKSARNSCWSKDAEYGLY

SIYQGGIFELKENDRIFVSVTNEHLIDMDHEASFFGAFLVGRS

Meso-TR3
(SEQ ID NO: 9)
MGIQGGSVLFGLLLVLAVFCHSGHSLQSYNPPRTDYKDDDDKQISGGGSEVEKTACPSG

KKARFJDESIFYKKWELEACVDAALLATQMDRVNAIPFTYEQLDVLKHKLDELYPQG

YPESVIQHLGYLFLKMSPEDIRKWNVTSLETLKALLEVNKGHEMSPQVATLIDRFVKGR

GQLDKDTLDTLTAFYPGYLCSLSPEELSSVPPSSIWAVRPQDLDTCDPRQLDVLYPKARL

AFQNMNGSEYFVKIQSFLGGAPTEDLKALSQQNVSMDLATFMKLRTDAVLPLTVAEVQ

KLLGPHVEGLKAEERHRPVRDWILRQRQDDLDTLGLGLQGLRTPPMILRTSEETISTVQE

KQQN1SPLVRERGPQRVAAHITGTRGRSNTLSSPNSKNEKALGRKINSWESSRSGHSFLS

NLHLRNGELVTHEKGFYYIYSQTYFRFQEEIKENTKNDKQMVQYIYKYTSYPDPILLMKS

ARNSCWSKDAEYGLYSIYQGGIFELKENDRIFVSVTNEHLrDMDHEASFFGAFLVGRSQ

NISPLVRERGPQRVAAHITGTRGRSNTLSSPNSKNEKALGRKJNSWESSRSGHSFLSNLHL

RNGELVIHEKGFYYIYSQTYFRFQEEIKENTKNDKQMVQYIYKYTSYPDPILLMKSARNS

CWSKDAEYGLYSIYQGGIFELKENDRIFVSVTNEHLIDMDHEASFFGAFLVGRSQNISPL

VRERGPQRVAAHITGTRGRSNTLSSPNSKNEKALGRKINSWESSRSGHSFLSNLHLRNGE

LVIHEKGFYYIYSQTYFRFQEEIKENTKNDKQMVQYIYKYTSYPDPILLMKSARNSCWS

KDAEYGLYSIYQGGIFELKENDRIFVSVTNEHLIDMDHEASFFGAFLVGRS

Meso-TR3HIS2Q
(SEQ ID NO: 10)
MGIQGGSVLFGLLLVLAVFCHSGHSLQSYNPPRTDYKDDDDKQISGGGSEVEKTACPSG

KKAREIDESLIFYKKWELEACVDAALLATQMDRVNAIPFTYEQLDVLKHKLDELYPQG

YPESVIQHLGYLFLKMSPEDIRKWNVTSLETLKALLEVNKGHEMSPQVATLIDRFVKGR

GQLDKDTLDTLTAFYPGYLCSLSPEELSSVPPSSIWAVRPQDLDTCDPRQLDVLYPKARL

AFQNMNGSEYFVKIQSFLGGAPTEDLKALSQQNVSMDLATFMKLRTDAVLPLTVAEVQ

KLLGPHVEGLKAEERHRPVRDWILRQRQDDLDTLGLGLQGLRTPPMILRTSEETISTVQE

KQQNISPLVRERGPQRVAAHITGTRGRSNTLSSPNSKNEICALGRKINSWESSRSGHSFLS

-continued

```
NLHLRNGELVIHEKGFYYIYSQTYFRFQEEIKENTKNDKQMVQYIYKYTSYPDPILLMKS

ARNSCWSKDAEYGLYSIYQGGIFELKENDRIFVSVTNEHLIDMDHEASFFGAFLVGRSQ

NISPLVRERGPQRVAAHITGTRGRSNTLSSPNSKNEKALGRKINSWESSRSGHSFLSNLHL

RNGELVIHEKGFYYTYSQTYFRFQEEIKENTKKDKQMVQYIYKYTSYPDPILLMKSARNS

CWSKDAEYGLYSIYQGGIFELKENDRIFVSVTNEHLIDMDHEASFFGAFLVGRSHHHHH

HQNISPLVRERGPQRVAAHITGTRGRSNTLSSPNSKNEKALGRK1NSWESSRSGHSFLSN

LHLRNGELVIHEKGFYYIYSQTYFRFQEEIKENTKNDKQMVQYIYKYTSYPDPILLMKSA

RNSCWSKDAEYGLYSIYQGGIFELKENDRIFVSVTNEHLIDMDHEASFFGAFLVGRS

Meso64-TR3
                                              (SEQ ID NO: 11)
MGIQGGSVLFGLLLVLAVFCHSGHSLQSYNPPRTDYKDDDDKQISGGGSEVEKTACPSG

KKAREIDESLIFYKKWELEACVDAALLATQMDRVNAIPFTYEQLDVLKHKLDELGGGS

GTPPMILRTSEETISTVQEKQQNISPLVRERGPQRVAAHITGTRGRSNTLSSPNSKNEKAL

GRKINSWESSRSGHSFLSNLHLRNGELVIHEKGFYYIYSQTYFRFQEEIKENTKNDKQMV

QYIYKYTSYPDPILLMKSARNSCWSKDAEYGLYSIYQGGIFELKENDRIFVSVTNEHUD

MDHEASFFGAFLVGRSQNISPLVRERGPQRVAAHITGTRGRSNTLSSPNSKNEKALGRKI

NSWESSRSGHSFLSNLHLRNGELVIHEKGFYYIYSQTYFRFQEEIKENTKNDKQMVQYIY

KYTSYPDPILLMKSARNSCWSKDAEYGLYSIYQGGIFELKENDRIFVSVTNEHLIDMDHE

ASFFGAFLVGRSQNISPLVRERGPQRVAAHITGTRGRSNTLSSPNSKNEKALGRKINSWE

SSRSGHSFLSNLHLRNGELVIHEKGFYYIYSQTYFRFQEEIKENTKNDKQMVQYIYKYTS

YPDPILLMKSARNSCWSKDAEYGLYSIYQGGIFELKBNDRIFVSVTNEHLIDMDHEASFF

GAFLVGRS

Meso64-TR3HIS2Q
                                              (SEQ ID NO: 12)
MGIQGGSVLFGLLLVLAVFCHSGHSLQSYNPPRTDYKDDDDKQISGGGSEVEKTACPSG

KKAREIDESLIFYKKWELEACVDAALLATQMDRVNAIPFTYEQLDVLKHKLDELGGGS

GTPPMILRTSEETISTVQEKQQNISPLVRERGPQRVAAHITGTRGRSNTLSSPNSKNEKAL

GRKINSWESSRSGHSFLSNLHLRNGELVIHEKGFYYIYSQTYFRFQEEIKENTKNDKQMV

QYIYKYTSYPDPILLMKSARNSCWSKDAEYGLYSIYQGGIFELKENDRIFVSVTNEHLID

MDHEASFFGAFLVGRSQNISPLVRERGPQRVAAHITGTRGRSNTLSSPNSKNEKALGRKI

NSWESSRSGHSFLSNLHUWGELVIHEKGFYYIYSQTYFRFQEEIKENTKNDKQMVQYIY

KYTSYPDPILLMKSARNSCWSKDAEYGLYSIYQGGIFELKENDRIFVSVTNEHLIDMDHE

ASFFGAFLVGRSHHHHHHQNISPLVRERGPQRVAAHITGTRGRSNTLSSPNSKNEKALG

RKINSWESSRSGHSFLSNLHLRNGELVIHEKGFYYIYSQTYFRFQEEIKENTKNDKQMVQ

YIYKYTSYPDPILLMKSARNSCWSKDAEYGLYSIYQGGIFELKENDRIFVSVTNEHLIDM

DHEASFFGAFLVGRS
```

EXAMPLES

The present teachings including descriptions provided in the Examples that are not intended to limit the scope of any claim or aspect. Unless specifically presented in the past tense, an example can be a prophetic or an actual example. The following non-limiting examples are provided to further illustrate the present teachings. Those of skill in the art, in light of the present disclosure, will appreciate that many changes can be made in the specific embodiments that are disclosed and still obtain a like or similar result without departing from the spirit and scope of the present teachings.

Example 1

Figure 2A:
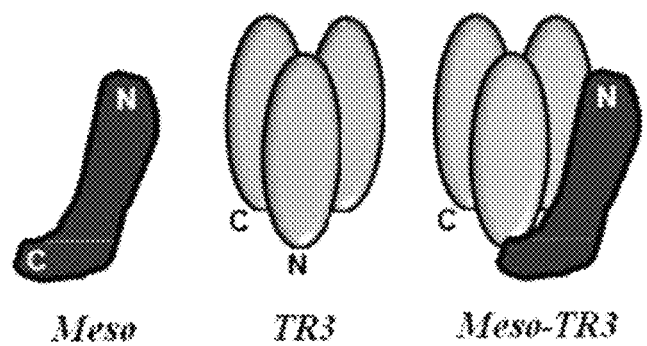
FIG. 2A-B illustrate design and biochemical characterization of MUC16-targeted TRAIL.
Figure 2B:
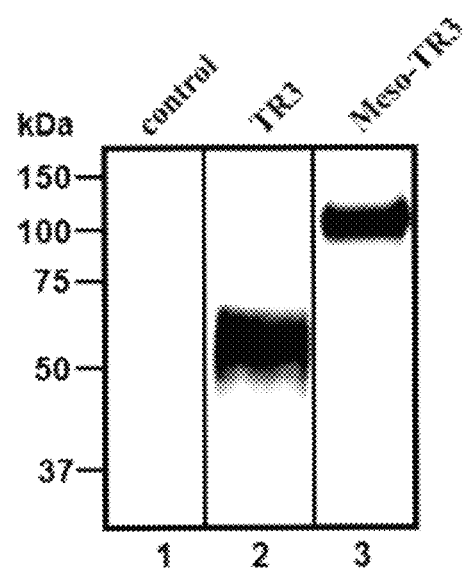

This example illustrates design and biochemical characterization of the MUC16-targeted TRAIL trimer TR3 (FIG. 2). FIG. 2A is a schematic representation of proteins developed by the inventors. In these experiments, soluble mesothelin (Meso) containing an N-terminal FLAG tag (not shown), the parental TRAIL drug platform TR3 (center) and the MUC16-targeted mesothelin-TR3 fusion protein (Meso-TR3) were produced by transient transfection of HEK293T cells. FIG. 2B, depicts a Western blot analysis (reducing conditions) documents the molecular weights of TR3 ($\approx$61 kDa, lane 2) and Meso-TR3 ($\approx$100 kDa, lane 3) using anti-TRAIL pAb. Supernatant from mock-transfected HEK293T cells served as a negative control (lane 1).

Soluble mesothelin has been shown to bind to MUC16 rapidly and with high affinity (Gubbels, J. A., et al., Mol. Cancer 5:50, 2006). Since endogenous mesothelin is attached to the cell surface via a GPI anchor (Hassan, R., et al., Clin. Cancer Res. 10:3937, 2004; Chang, K., et al., Proc. Natl. Acad. Sci. U.S.A. 93:136, 1996), we designed a secreted form of the glycoprotein by deleting its GPI signal sequence (FIG. 2A, Meso). For immunologic detection purposes, we included a FLAG epitope tag, located at the amino-terminus of the secreted protein (not shown). The recombinant protein was produced in HEK293T cells and Western blot analysis confirmed its identity with a molecular weight of $\approx$40 kDa (not shown). To convert TR3 (FIG. 2A, center) into a MUC16-targeted cancer drug, we inserted the entire cDNA of soluble mesothelin (including the N-terminal FLAG tag) to the 5'-terminus of a TR3 expression plasmid (FIG. 2A, Meso-TR3). The resulting genetic constructs were expressed in mammalian 293T cells and characterized by Western blot analysis. Meso-TR3 was identified as a fusion protein with an apparent molecular weight of $\approx$100 kDa with the parental molecule TR3 being $\approx$40 kDa smaller (FIG. 2B), consistent with the molecular weight of the mature and soluble form of human mesothelin.

Example 2

Figure 3A:
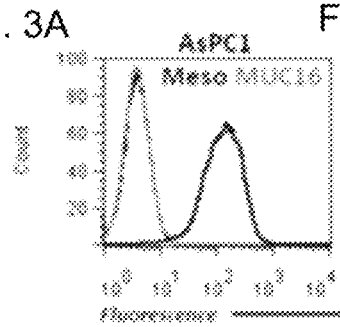
FIG. 3A-D illustrate expression levels of mesothelin and MUC16 in pancreatic cancer cell lines (A, B, C) and mesothelin binding to MUC16-expressing target cells (D).
Figure 3B:
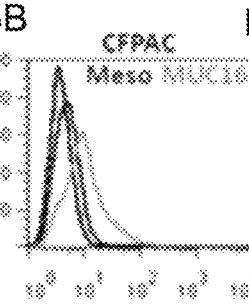
Figure 3C:
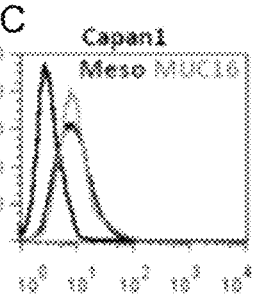

This example illustrates that mesothelin binds to MUC16 in MUC16-expressing cells. In these experiments, various cancer cell lines were screened for expression of mesothelin and MUC16. Briefly, cancer cell lines were incubated with antibodies against human mesothelin (K1, Santa Cruz) and human MUC16 (X75, AbCam). Primary antibody was detected with fluorescently labeled secondary antibody. The cells were then analyzed by flow cytometry. Mesothelin was expressed in all pancreatic cancer cell lines screened (AsPC1, CFPAC, Capan1) as well as ovarian cell line OVCAR3 (FIG. 3A-C, FIG. 4 A-C). MUC16 was only absent in AsPC3 (FIG. 3A). The presence of surface bound MUC16 is a prerequisite for the targeted delivery of TR3 to the cancer cells.

Figure 4A:
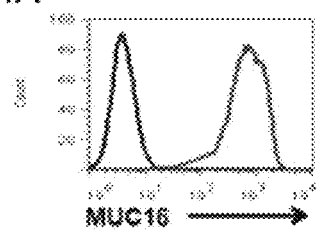

In order to confirm the MUC16 expression profile on OVCAR3 cells, we performed flow cytometry and were able to detect a strong surface expression with a homogenous staining pattern for 100% of the cells (FIG. 4A). Next, we tested the ability of soluble, FLAG-tagged mesothelin to bind to membrane-bound MUC16 employing an in vitro binding assay using the same OVCAR3 cell line. Indeed, flow cytometry confirmed that soluble mesothelin was capable of binding to OVCAR3 cells (FIG. 4B). The staining pattern correlated well with the MUC16 expression profile of this cell line as nearly 100% of the cells were positive for the FLAG epitope tag, i.e. bound recombinant mesothelin. This pilot experiment was crucial as it confirmed not only the binding of recombinant mesothelin to native MUC16 on the target cells but also demonstrated accessibility of the epitope tag in the context of the mesothelin/MUC16 interaction.

In a next step, we asked if mesothelin protein, as part of the Meso-TR3 fusion protein, was capable of interacting with MUC16 on the OVCAR3 cell surface to facilitate membrane tethering of TR3. It was predicted that the multi-domain Meso-TR3 fusion protein could bind to OVCAR3 cells via two discrete mechanisms: 1) via the mesothelin/MUC16 interaction and 2) via the TR3/death receptor interaction [both DR4 and DR5 are expressed in OVCAR3 cells, not shown and Reis, C. R., et al., Cell Death. Dis. 1:e83, 2010]. Since these circumstances would have complicated the interpretation of binding studies mediated exclusively via mesothelin, we first saturated the death receptor binding sites of Meso-TR3 with soluble death receptor 5 (DR5-Fc). In a following step, the Meso-TR3/DR5-Fc complexes were added to OVCAR3 cells in suspension. After several washing steps, the cells were stained for the presence of the FLAG epitope tag as evidence for drug binding to the OVCAR3 reporter cells. Using flow cytometry, we detected a strong and homogeneous fluorescence signal for cell-bound Meso-TR3, which was again nearly identical to the MUC16 staining profile and similar to the binding pattern of soluble mesothelin alone (FIG. 4C).

Further proof that Meso-TR3 and MUC16 do in fact co-localize on the plasma membrane of the target cells was obtained by employing confocal microscopy. Using the same detection system (anti-FLAG antibody) and death receptor blocking strategy (DR5-Fc pretreatment) as described above, the cells were now treated in an adherent state prior to washing, fixation, and immunostaining. Strong fluorescence signals were obtained for both the MUC16 eptiope (red) and the FLAG tag of Meso-TR3 (green) (FIG. 4D). Importantly, the two signals overlapped (FIG. 4D, "merge"), suggesting that Meso-TR3 co-localizes with the mesothelin receptor MUC16 on the cancer cell membrane.

Figure 3D:
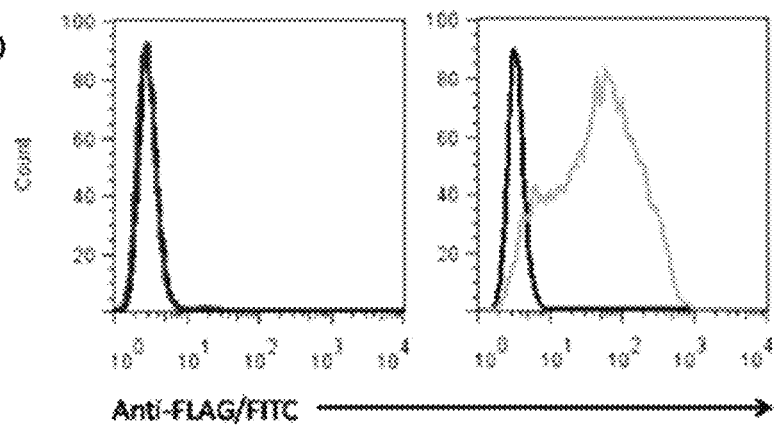

To demonstrate the targeting of mesothelin to cell surface MUC16, soluble FLAG-tagged mesothelin was generated in HEK293T cells. OVCAR3 cells were incubated with supernatant from HEK293T cells transfected with a secreted, FLAG-tagged form of human mesothelin. Following extensive washing to prevent detection of non-specific binding, mesothelin binding to MUC16 was assessed by staining for the FLAG tag. The cells were then analyzed by flow cytometry. There was a strong signal increase on the MUC16-positive OVCAR3 cancer cells, verifying that soluble mesothelin has a strong binding affinity for native MUC16 (FIG. 3D). In FIG. 4, A presents a FACS-analysis of OVCAR3 cells assessed for expression of MUC16 (mAb X75) and a PE-conjugated secondary Ab (red line). The secondary Ab alone served to establish the background fluorescence (black line). In experiments illustrated in B, OVCAR3 cells in suspension were incubated with HEK293T-derived culture supernatant containing soluble mesothelin. Mesothelin binding was detected via anti-FLAG antibody staining (mAb M2) and a FITC-conjugated secondary Ab (green line). Cells treated with culture medium alone served as negative control (black line). In experiments illustrated in C, OVCAR3 cells in suspension were incubated with HEK293T-derived culture supernatant containing Meso-TR3.

To prevent binding of Meso-TR3 via TR3/death receptor interaction, Meso-TR3 was complexed with soluble DR5-Fc. Meso-TR3 binding was detected via anti-FLAG antibody staining similar to (B) using mAb M2, followed by FITC-conjugated secondary Ab (green line). Cells treated with culture medium alone served as negative control (black line). D, OVCAR3 cells were grown on 4-chamber slides and incubated the following day with Meso-TR3 complexed with DR5-Fc, similar to what has been described for (C). After washing, the cells were stained with a mixture of MUC16 pAb (red) and FLAG mAb (green), respectively.

The cells were counterstained with TOPRO3 (blue, nuclei) and analyzed by confocal microscopy. The individual channels were overlaid to document co-localization of tumor marker and the targeted cancer drug (Merge). Original magnification: 63×.

Example 3

This example illustrates functional consequences of attaching the MUC16 targeting domain (mesothelin) to TR3.

TR3 and the fusion polypeptide mesothelin-TR3 (FIG. 1) were produced in HEK293T cells using standard transfection procedures. When MUC16-deficient Jurkat cells were treated with equimolar concentrations of TR3 and mesothelin-TR3, the cells were killed to the same degree (FIG. 5A).

In contrast, as shown in FIG. 5, when MUC16-high expressing OVCAR3 cells were treated with equimolar concentrations of TR3 and mesothelin-TR3, the mesothelin-TR3 was substantially more powerful in killing the cells than TR3 alone (5B).

OVCAR3 cells treated with mesothelin-TR3 can be rescued from cell death by adding increasing amounts of soluble mesothelin (5C). To determine whether cell death is caused by apoptosis, OVCAR3 cells were treated with mesothelin-TR3 in the presence of Z-VAD, a cell-permanent pan caspase inhibitor that inhibits the induction of apoptosis. In the presence of mesothelin-TR3, OVCAR3 cells were killed. However, with the addition of Z-VAD OVCAR3, cell death was minimal (5D).

To determine if the targeting of TR3 to the cell surface via mesothelin involves the native TR3 death pathway, OVCAR3 cells were treated with mesothelin-TR3 in the presence of increasing amounts of anti death receptor 5 (anti-DR5) antibody. Increasing amounts of anti-DR5 antibody inhibited the cancer cell killing by mesothelin-TR3, suggesting that the targeting of TR3 through mesothelin causes cell death via the native TR3 death pathway (5E).

Example 4

This example illustrates that mesothelin-TR3 is a targeted therapeutic on MUC16-expressing tumor cells, and that the mesothelin/MUC16 interaction can convert Meso-TR3 into a potent cancer drug (FIG. 6).

Figures 6A, 6B:
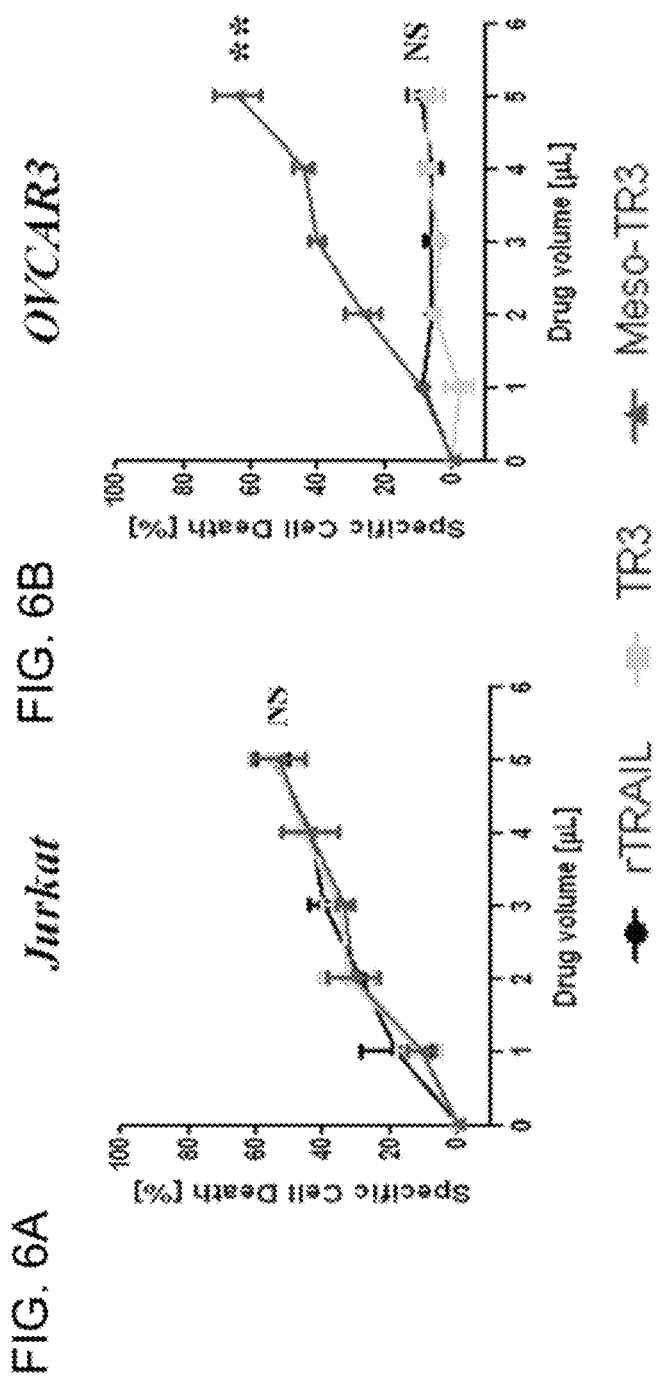
FIG. 6A-B illustrate that Meso-TR3 is a targeted therapeutic on MUC16-expressing tumor cells.

In order to compare the relative ability of cell death induction between Meso-TR3 and non-targeted TR3, it was important to establish the killing capacity of each drug mediated exclusively by the TR3 effector domain. Thus, we chose the TRAIL-sensitive T leukemia cell line Jurkat which lacks expression of MUC16 (not shown). We established the killing curves for both TR3 drugs and included recombinant TAIL (rTRAIL) as an internal reference. At the drug concentrations chosen, all TRAIL drugs induced cell death to the same degree in the absence of the tumor marker MUC16 (FIG. 6A). This killing profile changed significantly when the same drug concentrations were used to treat MUC16-positive OVCAR3 cells, known to be sensitive to recombinant TRAIL (Lane, D., et al., Gynecol. Oncol. 93:594, 2004; Lane, D., et al., Mol. Cancer Ther. 5:509, 2006; Reis. C. R., et al., Cell Death. Dis. 1:e83, 2010). Non-targeted TR3 turned out to be quite inefficient with only ≈10% cell killing capacity at the highest dose used (FIG. 6B). Importantly, TR3's killing profile was identical to that of rTRAIL, which is consistent with our earlier findings in that both drugs activate the extrinsic death pathway equally well and suggests that each trimer assumes the same native conformation (Spitzer, D., et al., Mol. Cancer Ther. 9:2142, 2010). Treatment with Meso-TR3, however, resulted in a much enhanced killing profile approaching 65% cell death at the highest drug dose employed (FIG. 6B). Linear regression analysis suggested a 7 to 12-fold stronger activity profile of Meso-TR3 when compared to TR3 and rTRAIL in OVCAR3 cells.

FIG. 6 shows the following: A, The cell killing profiles of TR3, Meso-TR3 and rTRAIL [0.2 ng/μL] were established on the MUC16-deficient T cell leukemia cell line Jurkat. NS, not significant (ANOVA). B, The same killing assay as in (A) using identical drug concentrations but the MUC16-positive ovarian cancer cell line OVCAR3 instead. **, P<0.006; NS, not significant (ANOVA).

Example 5

This example illustrates that Meso-TR3 is phenotypically identical to conventional TRAIL (FIG. 7).

Based on the much enhanced killing profile of Meso-TR3 on MUC16-positive OVCAR3 cells, we hypothesized that the mesothelin/MUC16 interaction, i.e. the surface tethering of Meso-TR3 was responsible for the observed effects. To investigate this assumption, we performed a killing assay in the presence of increasing concentrations of soluble mesothelin to block the MUC16/Meso-TR3 interaction. As predicted, we were able to achieve a dose-dependent reduction in cell killing from 80% (no competitor) to 40% (highest competitor dose) (FIG. 7A). We did not expect 100% rescue of the cells from apoptosis, because TR3 alone as well as recombinant rTRAIL exhibit baseline apoptosis-inducing activities in OVCAR3 cells, consistent with our observations.

In order to rule out phenotypic changes that might have been created following addition of the MUC16 targeting moiety mesothelin to the TR3 drug platform, we asked if the induction of cell death was purely mediated via the extrinsic death receptor pathway. Two lines of evidence suggest that this mechanism is well preserved following Meso-TR3 treatment. First, when soluble DR5-Fc was added to a standard killing assay using MUC16-positive OVCAR3 cells, Meso-TR3's killing capacity was nearly completely blunted, evidenced by a gradual decrease in cell death in a dose-dependent fashion from 90% in the absence of the soluble receptor to below 10% at the highest DR5-Fc concentration (FIG. 7B). As additional evidence for the involvement of the death receptor signaling cascade induced by Meso-TR3, the pan-caspase inhibitor Z-VAD-FMK blocked intracellular caspase activities and protected the cells completely from apoptosis (FIG. 7C).

Higher order TRAIL aggregates have been associated with increased activity due to more efficient death receptor clustering, especially regarding DR5 (Schneider, P., et al., J. Exp. Med. 187:1205, 1998.). In an attempt to recapitulate these observations, we treated Jurkat cells with Meso-TR3 in the presence of a mAb directed against the mesothelin moiety of the MUC16-targeted fusion protein. Using a sublethal dose of Meso-TR3 (33% cell death), we were able to demonstrate a dose-dependent augmentation of cell death to nearly 100% at the highest concentration of cross-linking antibody (FIG. 7D). These results strongly suggest that Meso-TR3 assumes a monomeric configuration in solution that can be further functionally enhanced by forming higher order aggregates (dimers), a concept just recently being utilized to treat highly vascularized cancers (Wilson, N. S., et al., Cancer Cell 22:80, 2012).

In FIG. 7, A, OVCAR3 cells were challenged with a constant amount of Meso-TR3 (80% specific cell death) and increasing concentrations of soluble mesothelin to study the impact of the mesothelin/MUC16 interaction of Meso-TR3. B, OVCAR3 cells were challenged with a constant amount of Meso-TR3 (90% specific cell death) and increasing concentrations of DR5-Fc to verify involvement of the extrinsic death pathway as a mechanism of Meso-TR3 killing. C, OVCAR3 cells were treated with a constant amount of Meso-TR3 (75% specific cell death) in the presence of Z-VAD-FMK, a pan-caspase inhibitor to block the extrinsic death pathway. Cells treated with DMSO were used as a control. D, MUC16-deficient Jurkat cells were treated with low dose Meso-TR3 (33% specific cell death) in the presence of anti-mesothelin mAb. Cross-linking of Meso-TR3 enhances target cell death to nearly 100%. Cells treated with anti-mesothelin Ab alone served as a control. Cells treated with medium alone were used as control. Error bars, ±SD. Results are representatives of at least 2 independent experiments done in triplicates.

Example 6

Figure 8A:
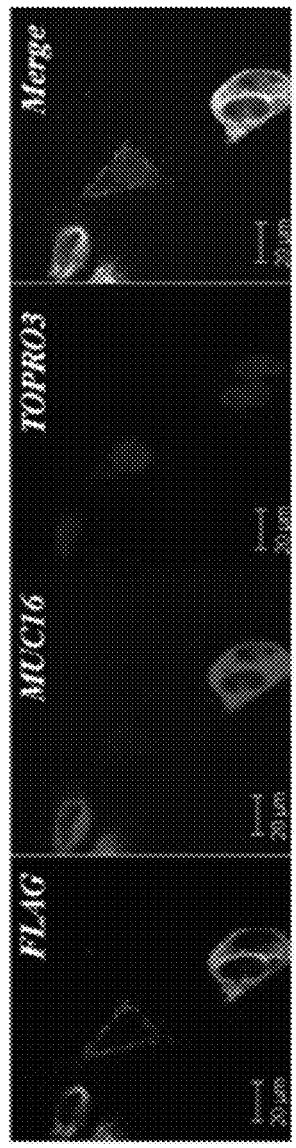
FIG. 8A-B illustrate selective killing of MUC16-expressing tumor cells by a mesothelin-TR3 fusion polypeptide.
Figure 8B:
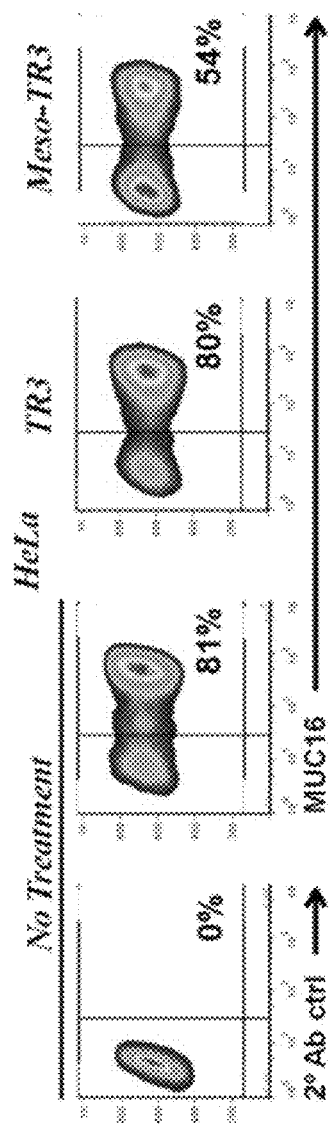

This example illustrates that mesothelin-TR3 selectively kills MUC16-expressing cells. In order to study drug selectivity aspects of Meso-TR3 toward MUC16-expressing targets, we took advantage of the fact that HeLa cells are composed of a native mix of MUC16-positive and negative cells (80% and 20%, respectively). We therefore performed confocal microscopy on HeLa targets for tethering Meso-TR3. And indeed, those cells positive for the MUC16 tumor marker were heavily coated with Meso-TR3 (FIG. 8A). However, cells with a low or absent antigen expression were incapable of capturing Meso-TR3 and stained only weakly for the targeted drug (FIG. 8A, arrow). Based on these findings, we anticipated that Meso-TR3 would have a higher affinity for the MUC16-positive population within the mix and selectively eliminate these from the cell pool. And indeed, Meso-TR3 treatment resulted in a more than 30% reduction of MUC16-positive cells from 80% to 54% (FIG. 8B). In contrast, non-targeted TR3 was incapable of shifting the MUC16 ratio in this cervical cancer cell line due to the fact that it cannot discriminate between the two cell populations.

In these experiments (FIG. 8), HeLa cells were grown on 4-chamber slides and incubated the following day with Meso-TR3 complexed with DR5-Fc (8A). After washing, the cells were stained with a mixture of MUC16 pAb (red) and FLAG mAb (green), respectively. The cells were counterstained with TOPRO3 (blue, nuclei) and analyzed by confocal microscopy. The individual channels were overlaid to document co-localization of tumor marker and the targeted cancer drug (Merge). Original magnification: 63×. B, HeLa cells were treated with TR3 and Meso-TR3 for 24 h. Two days post-treatment, the cells were assessed for changes in the MUC16 ratio using flow cytometry. Representative density plots are shown from experiments done at least twice in duplicates. These data indicate that Mesothelin-TR3 is more potent against MUC16-positive cells compared to TR3 alone.

Example 7

Figure 9A:
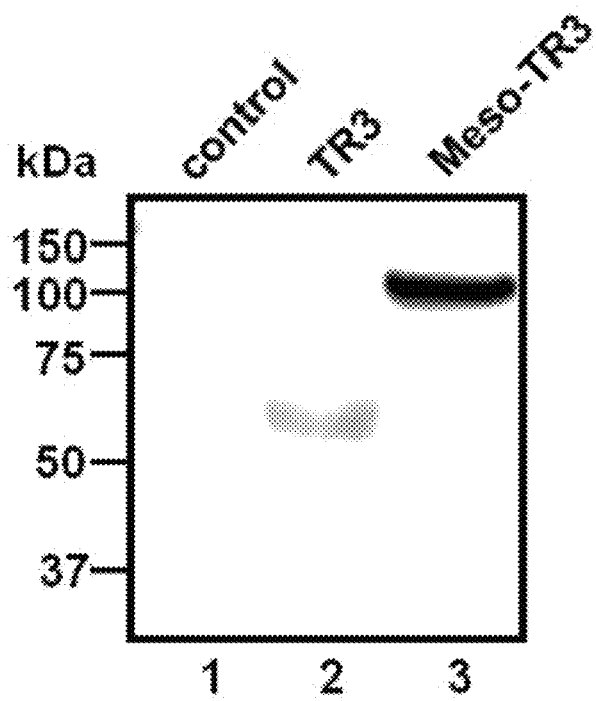
FIG. 9A-B illustrate that Meso-TR3 is fully activated on tumor cells expressing the biomarker MUC16.
Figure 9B:
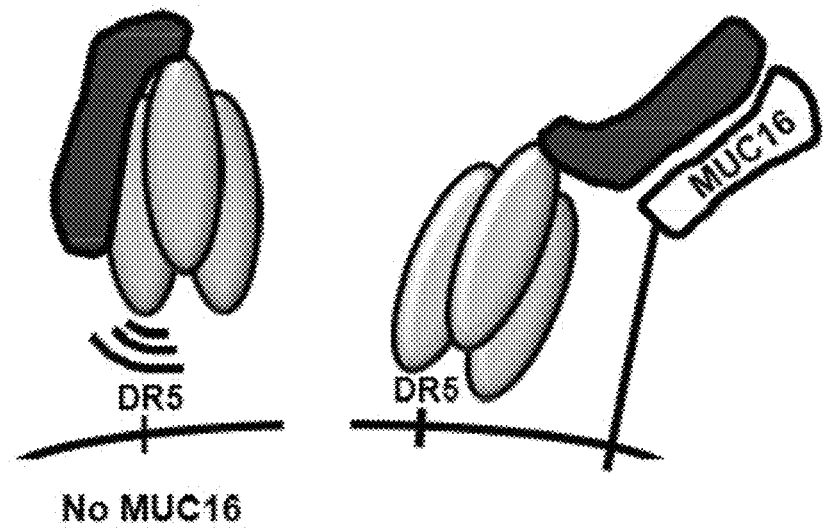
Figure 10:
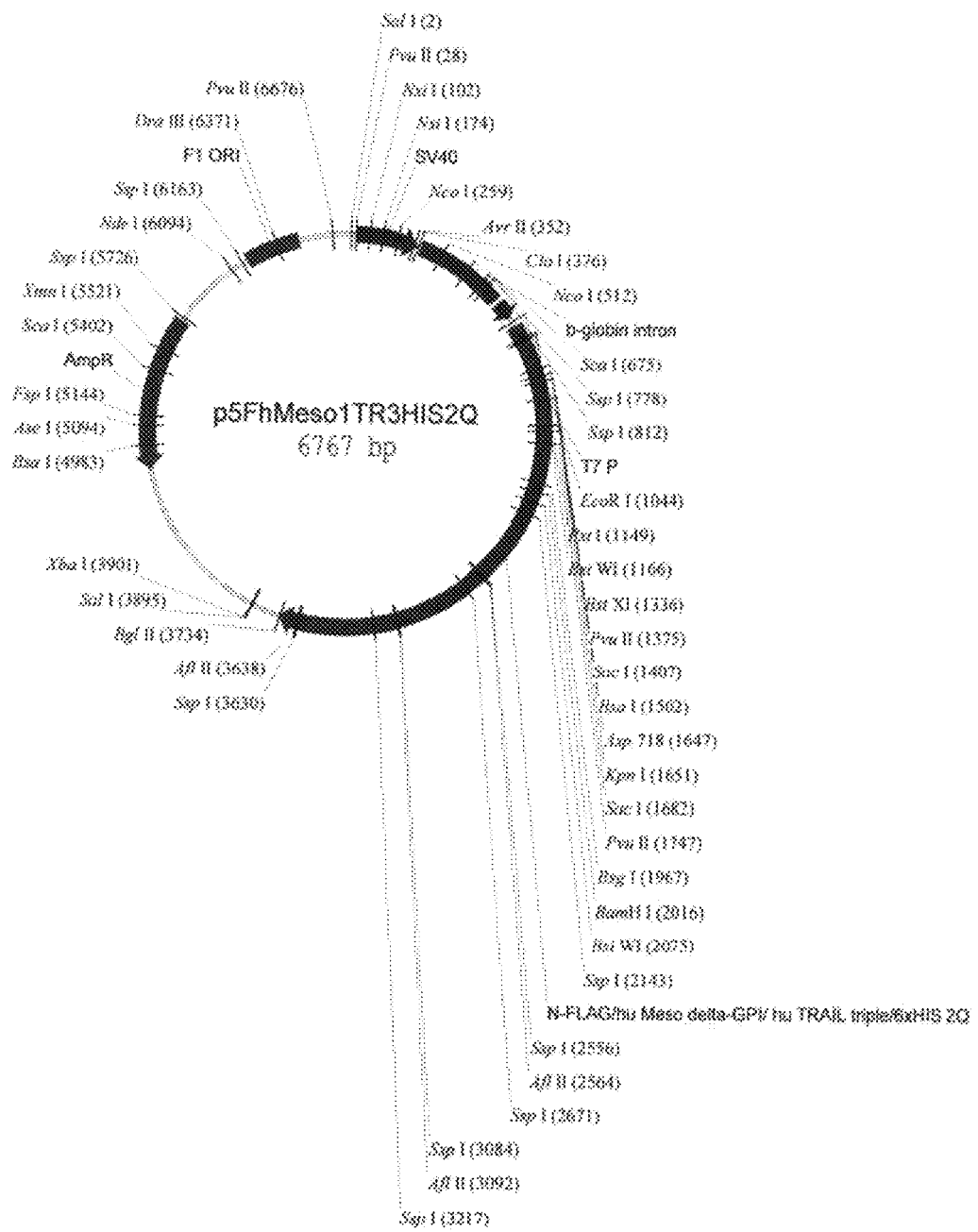
FIG. 10 illustrates a restriction map of plasmid p5FhMeso64TR3HIS2Q.

This example illustrates that Meso-TR3 is a cancer drug with prodrug properties and is fully activated on tumor cells expressing the biomarker MUC16 (FIG. 9).
Since the activity profiles of our TR3 drugs were routinely determined via functional apoptosis assays on reporter cells that lack the tumor marker MUC16 (compare FIG. 6A), we wanted to confirm that the drug input was similar for the respective TR3 variant. In order to do this, we employed semi-quantitative Western blot analysis, a detection method that does not rely on a native protein conformation, such as a TRAIL ELISA. When drug concentrations were analyzed that achieved identical killing capacities on MUC16-negative Jurkat cells, we consistently found much stronger signal intensities for Meso-TR3 compared to TR3 with a ratio of ≈8 in favor of Meso-TR3 (FIG. 9A). These results suggest that, compared to TR3 alone, a significantly higher concentration of Meso-TR3 is required to achieve equivalent biological effects on MUC16-deficient cells (FIG. 9B).

In these experiments (FIG. 9), TR3 and Meso-TR3 preparations exerting identical killing profiles on MUC16-deficient tumor cells (A, compare with FIG. 6A) were subjected to semi-quantitative Western blot analysis under reducing conditions using anti-TRAIL pAb. The immunoreactive bands were quantified using QuantityOne® software (Bio-Rad, Hercules, Calif.) on a BioRad imaging system, with Meso-TR3 approximately 8-fold more abundant than TR3. B, Hypothetical proposed mechanism of Meso-TR3 activity. Without being limited by theory, the inventor have developed a hypothetical model. In this model, the mesothelin moiety of Meso-TR3 can partially interfere with an unrestricted interaction of the TR3 domain and its death receptors (left panel). In the presence of MUC16 on the cancer cell surface, the mesothelin targeting domain can be removed from the TR3 surface thus enabling unrestricted access to and full activation of the death receptor-mediated extrinsic death pathway (right panel).

Example 8

These experiments, depicted in FIG. 12, illustrate that Meso-TR3 reduces the tumor burden in an in vivo mouse model of ovarian cancer. As shown in FIG. 12: A, ovarian cancer cell line OVCAR3 was genetically engineered, via retroviral infection, to stably express the luciferase-YFP fusion protein with a transduction efficiency of 24% (left panel, "Pre-sort", along with the corresponding luciferase activity following addition of luciferin subsrate). In order to enrich the luciferase expressing cells, FACS sort was performed, resulting in a stable cell pool with more than 93% YFP (luciferase)-positive cells (right panel, Post-sort", along with the corresponding luciferase activity following addition of luciferin subsrate). B, Meso-TR3 and the parental TR3 protein preparations were tested in apoptosis assays and show similar killing activity on MUC16-negative Jurkat cells (left panel). The same protein preparations were than applied to MUC6-positive OVCAR3 cells (adherent) and document the much increased killing profile of Meso-TR3 compared to the non-targeted TR3 parental molecule (right panel). C, OVCAR3 cell were first non-enzymatically detached from the culture flasks using EDTA and treated in suspension with TR3 and Meso-TR3 at equipotent concentrations on Jurkat cells (compare B, left panel). The cells were allowed to settle and the surviving cells that adhered following drug treatment were stained 2 days later with crystal violet. Of note, Meso-TR3 almost completely eliminated the cancer cells, in agreement to what has been documented above when the cells were treated in an adherent state (B, right panel). FIG. 12 D and FIG. 13: for the functional assessment of MUC16-targeted Meso-TR3 in vivo, SCID mice were injected i.p. with 1×106 YFP-sorted OVCAR3 cells (93%). The next day, luciferase expression was monitored via non-invasive whole animal imaging and the mice were treated for 7 days with equivalent doses of TR3 and Meso-TR3 via the i.p. route and imaged at the indicated intervals. Of note, only the mouse treated with Meso-TR3 showed a substantial decrease in signal intensity, which was nearly 150-fold less than the initial luciferase activity and suggests enhanced and selective elimination of the labeled cells from the peritoneal location. In contrast, in mice treated with medium alone (ctrl) and TR3, the signal intensity did not change and support the results obtained from in vitro killing experiment.

Example 9

Figure 13A:
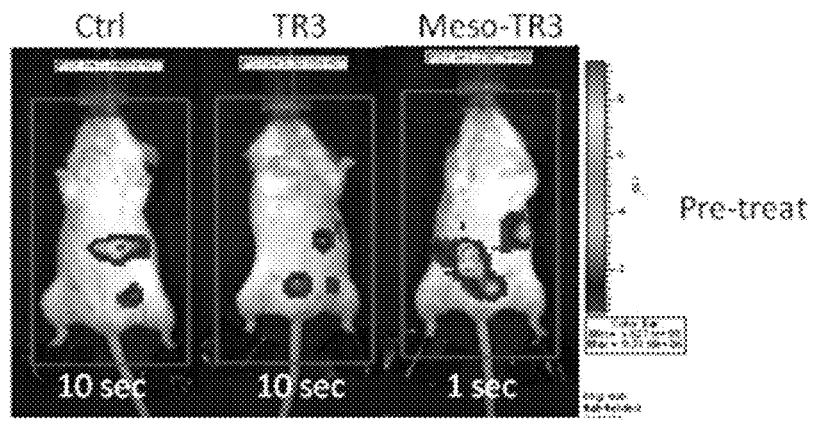
FIG. 13A-C illustrate examples of reduction of tumor burden by Meso-TR3 in an in vivo model of ovarian cancer.
Figure 13B:
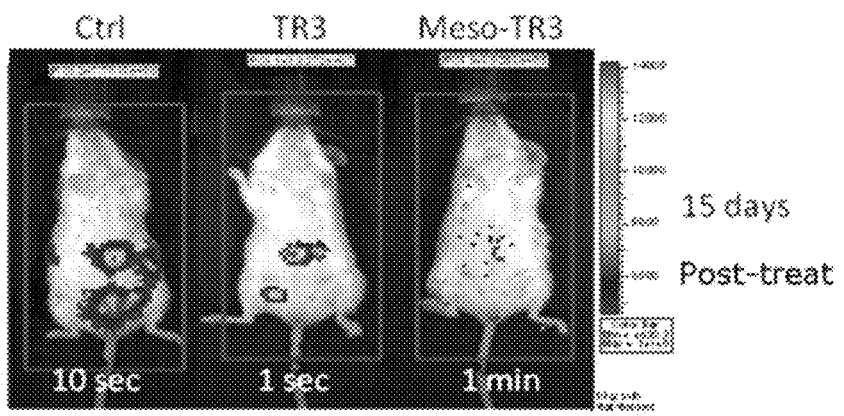
Figure 13C:
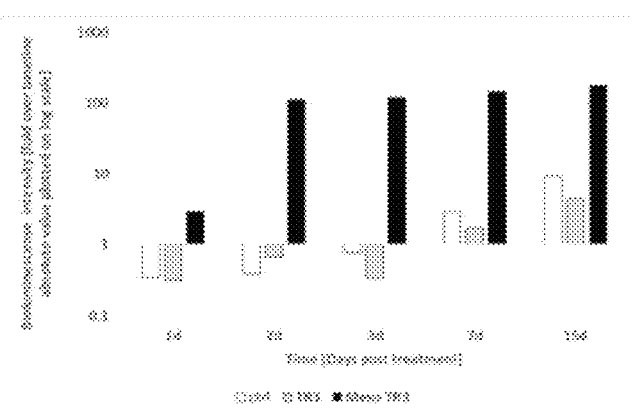

These experiments, depicted in FIG. 13 illustrate that Meso-TR3 reduces the tumor burden in an in vivo mouse model of ovarian cancer.

In these experiments, animals bearing MUC16-positive tumors expressing the luciferase-YFP fusion protein (as in Example 8) were treated with TR3, Meso-TR3, or control.

FIG. 13 illustrates examples of model animals treated with TR3, Meso-TR3, or control. Control, TR3 and Meso-TR3 treated animals bearing ovarian cancer cell line OVCAR3 were imaged at the indicated times. In FIG. 13, A illustrates luciferase intensities prior to treatment, whereas B illustrates luciferase intensities 15 days post-treatment. Times beneath animals in A and B indicate duration of camera exposures. C illustrates a dramatic drop in image intensity in the animal receiving Meso-TR3 at 15 days. Note low level of signal obtained 15 days post-treatment in an animal which received Meso-TR3 even after a 1 min. camera exposure (B), whereas an animal receiving TR3 or control had much greater signals 15 days post-treatment. Data is normalized for photons/second. These data demonstrate therapeutic effectiveness of meso-TR3 against tumors including MUC16-positive tumors.

Example 10

This example illustrates production and killing potential of TR3, Meso64-TR3, and Meso-TR3. In these experiments, a Titer-Glo® assay (Promega Corporation, Madison, Wis.) was used in accordance with the supplier's instructions.

As shown in FIG. 14, the present inventors have demonstrated production in vitro of TR3, meso64-TR3, and Meso-TR3 (Western blot in upper panel). The present inventors also show the potency of Meso64-TR3 for killing Ovcar-3 ovarian cancer cells, and the even greater potency of Meso1-TR3 for killing Ovcar-3 ovarian cancer cells (cell killing curve in lower panel).

All references cited are hereby incorporated by reference, each in its entirety.

What is claimed is:

1. A fusion polypeptide comprising:
   a mesothelin polypeptide selected from the group consisting of meso64 and mesothelinΔGPI; and
   three consecutive extracellular domains of TNF-related apoptosis-inducing ligand (TRAIL) domains fused together in a head-to-tail configuration.

2. A fusion polypeptide in accordance with claim 1, wherein the mesothelin polypeptide is meso64.

3. A fusion polypeptide in accordance with claim 1, wherein the mesothelin polypeptide is mesothelinΔGPI.

4. A fusion polypeptide in accordance with claim 1, further comprising a His-tag.

5. An anticancer therapeutic comprising the fusion polypeptide of claim 1.

6. A nucleic acid comprising a sequence encoding the fusion polypeptide of claim 1.

7. A vector comprising the nucleic acid of claim 6.

8. A vector of claim 7, wherein said vector is a plasmid.

9. A method of inducing apoptosis in a tumor cell, comprising contacting the tumor cell with the fusion polypeptide of claim 1.

10. The method of claim 9, wherein the tumor cell expresses MUC16.

11. The method of claim 9, wherein the tumor cell is an ovarian cancer cell.

12. The method of claim 9, wherein the tumor cell is a pancreatic cancer cell.

13. The method of claim 9 wherein the tumor cell is a breast cancer cell.

14. A method of treating a cancer in a subject in need thereof, the method comprising administering to the subject a therapeutically effective amount of the fusion polypeptide of claim 1.

15. The method of claim 14, wherein the cancer comprises MUC16-positive cells.

16. The method of claim 14, wherein the cancer comprises ovarian cancer cells.

17. The method of claim 14, wherein the cancer comprises pancreatic cancer cells.

18. The method of claim 14, wherein the cancer comprises breast cancer cells.

* * * * *

UNITED STATES PATENT AND TRADEMARK OFFICE
CERTIFICATE OF CORRECTION

PATENT NO. : 9,815,882 B2  
APPLICATION NO. : 14/798045  
DATED : November 14, 2017  
INVENTOR(S) : Dirk Spitzer et al.

It is certified that error appears in the above-identified patent and that said Letters Patent is hereby corrected as shown below:

In the Specification

Column 1, Line 20 should read:
This invention was made with government support under CA150945 awarded by the National Institutes of Health. The government has certain rights in the invention.

Signed and Sealed this
Nineteenth Day of February, 2019

Andrei Iancu
*Director of the United States Patent and Trademark Office*